US011555196B2

(12) United States Patent
Meyers et al.

(10) Patent No.: US 11,555,196 B2
(45) Date of Patent: Jan. 17, 2023

(54) CO-EXPRESSION OF HUMAN CHAPERONE PROTEINS IN PLANTS FOR INCREASED EXPRESSION OF HETEROLOGOUS POLYPEPTIDES

(71) Applicant: University of Cape Town, Cape Town (ZA)

(72) Inventors: Ann Elizabeth Meyers, Plumstead (ZA); Edward Peter Rybicki, Cape Town (ZA); Emmanuel Aubrey Margolin, Rondebosch (ZA)

(73) Assignee: UNIVERSITY OF CAPE TOWN, Rondebosch (ZA)

( * ) Notice: Subject to any disclaimer, the term of this patent is extended or adjusted under 35 U.S.C. 154(b) by 0 days.

(21) Appl. No.: 16/618,704

(22) PCT Filed: Jun. 1, 2018

(86) PCT No.: PCT/IB2018/053944
§ 371 (c)(1),
(2) Date: Dec. 2, 2019

(87) PCT Pub. No.: WO2018/220595
PCT Pub. Date: Dec. 6, 2018

(65) Prior Publication Data
US 2021/0147860 A1 May 20, 2021

(30) Foreign Application Priority Data
Jun. 2, 2017 (GB) ..................................... 1708866

(51) Int. Cl.
*C12N 15/82* (2006.01)
(52) U.S. Cl.
CPC ..... *C12N 15/8216* (2013.01); *C12N 15/8258* (2013.01)
(58) Field of Classification Search
None
See application file for complete search history.

(56) References Cited

U.S. PATENT DOCUMENTS

2014/0127749 A1* 5/2014 Mason ................ C07K 16/109
435/69.1

FOREIGN PATENT DOCUMENTS

| WO | WO 2005/010046 A1 | 2/2005 |
| WO | WO 2009/076778 A1 | 6/2009 |
| WO | WO 2011/011495 A1 | 1/2011 |
| WO | WO 2012/145759 A2 | 10/2012 |

OTHER PUBLICATIONS

Ciplys et al. (FEMS Yeast Research, 2011, 11(6): 514-523).*
Teng, C-Y, et al., "α-Synuclein and β-Synuclein Enhance Secretion Protein Production in Baculovirus Expression Vector System", Appl. Microbiol. Biotechnol., v. 97, p. 3875-3884 (2013).
Alibolandi, M., et al., "Improving Recombinant Protein Solubility in *Escherichia Coli*: Identification of Best Chaperone Combination which Assists Folding of Human Basic Fibroblast Growth Factor", African J. of Biotech., v. 9, No. 47, p. 8100-8109 (Nov. 22, 2010).
Ciplys, E., et al., "Overexpression of Human Calnexin in Yeast Improves Measles Surface Glycoprotein Solubility", Fems Yeast Research, v. 11, n. 6, p. 514-523, (Jun. 27, 2011).
Macdonald, J. et al., "Co-Expression with the Type 3 Secretion Chaperone CesT from Enterohemorrhagic *E. Coli* Increases Accumulation of Recombinant Tir in Plant Chloroplasts", Frontiers in Plant Science, v. 8, p. 283 (Mar. 6, 2017).
Ashraf, S. et al. "High level expression of surface glycoprotein of rabies virus in tobacco leaves and its immunoprotective activity in mice", 2005, Journal of Biotech., vol. 119, pp. 14.
Azoun, S.B. et al. "Expression of rabies virus glycoprotein in the methylotrophic yeast *Pichia pastoris*", 2017, Biotech. & Applied Biochem, pp. 12.
Askri, H., et al. "Production, purification, and characterization of recombinant rabies virus glycoprotein expressed in PichiaPink™ yeast", 2022, Biotechnology Reports, pp. 12.
Dolittle, R.F. et al. "Determining Divergence Times of the Major Kingdoms of Living Organisms with a Protein Clock", 1996, Science, vol. 271, pp. 8.
Kelleher D.J. et al. "An evolving view of the eukaryotic oligosaccharyltransferase", 2006, Glycobiology, vol. 16, pp. 16.
Ponndorf D. et al "Plant-made dengue vims-like particles produced by coexpression of structural and non-structural proteins induce a humoral immune response in mice", 2021, Plant Biotech., vol. 19, pp. 12.
Sakamoto S. et al. "Studies on the structures and antigenic properties of rabies virus glycoprotein analogues produced in yeast cells", 1999, Vaccine, vol. 17, pp. 14.
Sugrue R.J. et al. "Expression of the dengue virus structural proteins in Pichia pastoris leads to the generation of virus-like particles" 1997, Journal of Gen. Virology, vol. 78, pp. 6.
Webster D.E. et al. "The development of a plant-based vaccine for measles", 2005, Vaccine, vol. 23, pp. 7.
Webster D.E. et al. "Measles virus hemagglutinin protein expressed in transgenic lettuce induces neutralizing antibodies in mice following mucosal vaccination", 2006, Vaccine, vol. 24, pp. 7.

* cited by examiner

*Primary Examiner* — Charles Logsdon

(57) ABSTRACT

The present invention relates to a method for increasing the expression and/or promoting correct folding of a heterologous polypeptide of interest in a plant cell, comprising co-expressing the heterologous polypeptide of interest with a polypeptide encoding a mammalian chaperone protein. The invention also relates to plant cells and plants, which either transiently or stably, co-express the heterologous polypeptide of interest and the chaperone protein.

14 Claims, 10 Drawing Sheets

Specification includes a Sequence Listing.

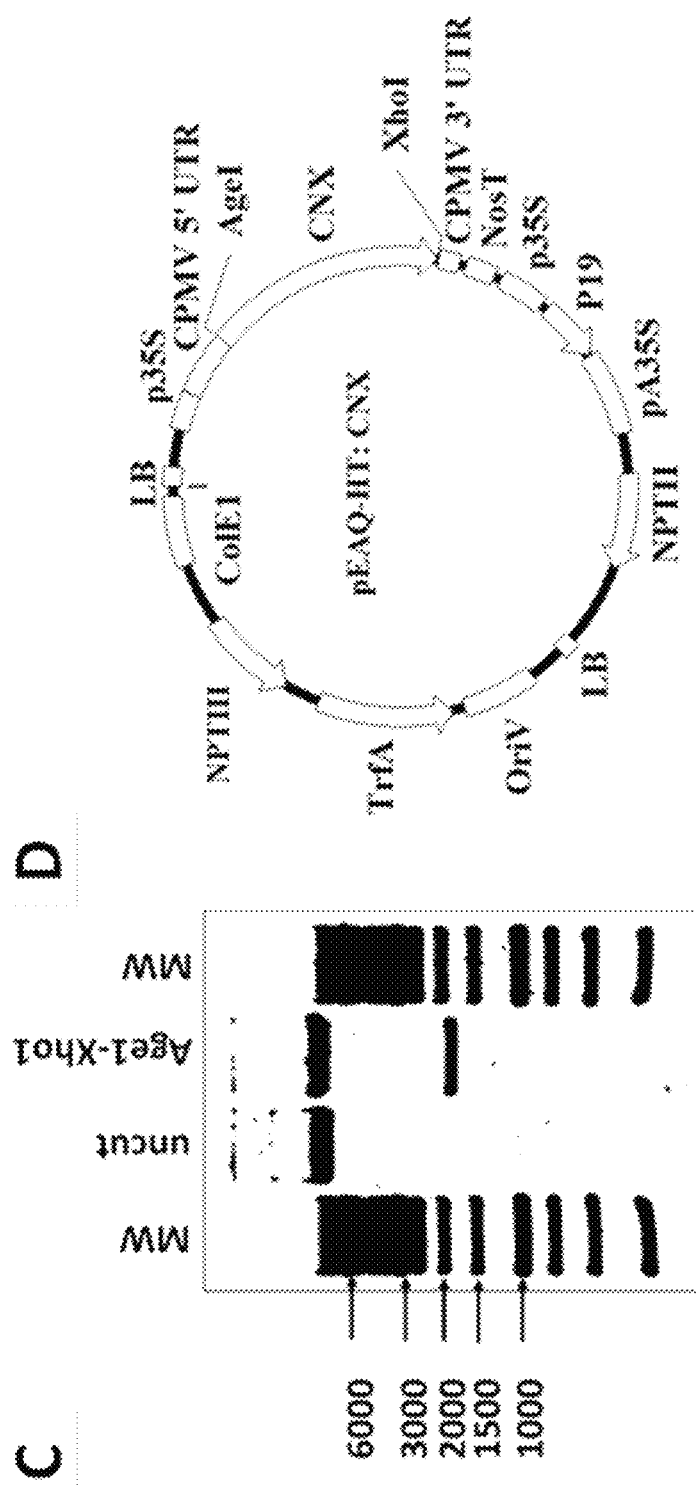
Figure 3 contd.

CO-EXPRESSION OF HUMAN CHAPERONE PROTEINS IN PLANTS FOR INCREASED EXPRESSION OF HETEROLOGOUS POLYPEPTIDES

CROSS-REFERENCE TO RELATED APPLICATIONS

This application is a U.S. National Phase of International Application Serial No. PCT/IB2018/053944 filed on Jun. 1, 2018, which claims priority to United Kingdom Patent Application No. GB 1708866.7 filed on Jun. 2, 2017, both of which are hereby incorporated herein by reference for all purposes.

BACKGROUND OF THE INVENTION

This invention relates to a method for increasing the expression and/or promoting the correct folding of a heterologous polypeptide of interest in a plant cell, wherein the method comprises co-expressing the heterologous polypeptide of interest with a polypeptide encoding a mammalian chaperone protein. The invention further relates to plant cells and plants which, either transiently or stably, co-express the heterologous polypeptide of interest and the mammalian chaperone protein.

Conventional pharmaceutical production platforms are increasingly unable to meet global demands due to limitations in terms of scalability, long production times and high costs. In recent years, plants have gained attention as a potentially cheap and scalable system for the production of heterologous proteins that is particularly suited to the needs of developing countries. Plant-based expression systems are especially appealing to resource limited countries due to the lower raw material and infrastructure cost requirements which often pose formidable barriers to entry. The commercial viability of any plant-made pharmaceutical is largely governed by the expression yield which generally needs to exceed 1% of the total soluble protein. This threshold however is seldom realized and expression levels remain a challenge for many heterologous proteins, particularly viral glycoproteins (Margolin et al, submitted for publication). Instead, a threshold of 50 mg/kg has inadvertently become the gold standard after the development of a plant-produced influenza haemagglutinin candidate for clinical trials by Medicago (D'Aoust et al., 2008; Landry et al., 2010).

The invention encompasses the co-expression of the human molecular chaperones (calreticulin, calnexin, GRP78/BiP, protein disulphide isomerase and/or ERp57) in plants to improve the expression of heterologous glycoproteins. The present inventors have demonstrated the utility of this approach using an engineered soluble HIV Envelope glycoprotein as a model antigen and subsequently demonstrated the broader applicability of this approach. This is the first report to describe the co-expression of a heterologous chaperone in planta to improve the production of a recombinant protein. Based on 3 independent experiments, the relative expression of the HIV Envelope gp140 glycoprotein was improved 12.7-fold by calreticulin (CRT) co-expression and 1.17 fold by calnexin (CNX) co-expression respectively. The inventors have further demonstrated that this approach is broadly applicable to other glycoproteins by showing a similar effect for a soluble Rift Valley Fever virus glycoprotein, a near full-length HIV Envelope glycoprotein and an antibody. The inventors propose that many viral glycoproteins may be incompatible with the endogenous plant chaperones due to the divergent evolution of plants and mammalian hosts for common pathogens. The co-expression of a heterologous glycoprotein with its cognate chaperone described herein establishes a new paradigm for the production of viral glycoproteins in plants. This approach is broadly applicable to other heterologous proteins, especially those usually produced in mammalian expression systems such as mammal-infecting viruses, and could potentially enable the production of low yielding vaccine antigens, or other reagents or diagnostic proteins, at commercially viable levels.

Given that expression yields in plants are often the deciding factor that limits the viability of plant-made proteins or plant-made pharmaceuticals, strategies to improve production levels and/or folding are of considerable interest. A recent trend to improve the yield and quality of plant made pharmaceuticals (PMPs) has resulted in extensive efforts to manipulate the plant host cell environment beyond just the expression of the heterologous protein of choice. This has been most widely used to address differences in the plant-glycosylation machinery compared to conventional expression platforms.

Recently, the co-expression of companion protease inhibitors have shown promise to mitigate the effects of endogenous plant proteases in planta during expression and ex planta during purification. Notably, co-expression of tomato cystatins (S/CYS8 and S/CYS9) and tomato cathepsin D inhibitor were reported to increase the accumulation of a prototype monoclonal antibody migrating towards the leaf apoplast, although this effect may be less profound in older leaves. The use of gene knockdown has also garnered attention to mitigate the harmful effects of specific proteases, however the central role of proteases in growth and development complicates this approach. Recently D'Aoust and colleagues reported that the co-expression of the influenza M2 ion channel significantly improved the yields of recombinant influenza haemagglutinin antigen in N. benthamiana (Jutras et al., 2015). Lastly, the protease furin has been co-expressed in N. benthamiana to enable the production of biologically active transforming growth factor-β1 (Wilbers et al., 2016). These examples highlight the remarkable plasticity of the plant proteome which can be manipulated for the production of high levels of pharmaceutically-relevant proteins. To our knowledge, no study has addressed the impact of co-expressing heterologous mammalian chaperones in planta to improve the production of a recombinant protein in terms of both yield and protein folding. This approach represents a new paradigm for the production of high yields of heterologous glycoproteins in plants.

SUMMARY OF THE INVENTION

The present invention relates to a method for increasing the expression of a heterologous polypeptide of interest in a plant cell, wherein the method comprises co-expressing the heterologous polypeptide of interest with a polypeptide encoding a mammalian chaperone protein.

In a first aspect of the invention there is provided for a method of increasing the expression and/or promoting the correct folding of a heterologous polypeptide of interest in a plant cell, wherein the method comprises the steps of: (i) providing a first nucleic acid encoding a mammalian chaperone protein, (ii) providing a second nucleic acid encoding a heterologous polypeptide of interest, (iii) cloning the first and second nucleic acids into at least one expression vector adapted to express a polypeptide in a plant cell, (iv) transforming or infiltrating a plant cell with the at least one expression vector of step (iii), (v) co-expressing the heterologous polypeptide of interest and the polypeptide encoding the mammalian chaperone protein in the plant cell, and (vi) recovering the polypeptide of interest from the plant cell. It will be appreciated by those of skill in the art that the transformation may be either transient or stable transformation of the plant cell.

In a first embodiment of the invention the mammalian chaperone protein is a human chaperone protein. Further, at least one human chaperone protein is expressed in the plant cell and is preferably selected from the group consisting of calnexin, calreticulin, GRP78/BiP, GRP94, GRP170, HSP47, ERp29, protein disulfide isomerase, peptidyl prolyl cis-trans-isomerase and ERp57. Preferably, the human chaperone protein is selected from calnexin, calreticulin, GRP78/BiP, protein disulphide isomerase and/or ERp57.

In a second embodiment of the invention the heterologous polypeptide of interest is a glycoprotein. Alternatively, the heterologous polypeptide of interest may be a non-glycosylated protein. The heterologous polypeptide of interest may be a polypeptide from a virus, including Bunyaviruses such as Rift Valley fever virus, Crimean Congo haemorrhagic fever virus, Flaviviruses such as West Nile Virus and Zika virus, Orthomyxoviruses, Togaviruses such as Chikungunya virus, Lentiviruses such as HIV, Herpes viruses such as Epstein Barr virus, Herpes Simplex virus-1, Herpes Simplex virus-2, Filoviruses such as Ebola virus and Marburg virus, Hantaviruses such as Sin Nombre virus, or Henipaviruses such as Nipah virus amongst others. The virus may further infect any vertebrate host.

In a third embodiment of the invention expression of the heterologous polypeptide of interest in the plant cell is increased relative to a control plant cell which has only been transformed with the heterologous polypeptide of interest. Further, the folding of the heterologous polypeptide of interest when co-expressed with the mammalian chaperone protein may be closer to the folding of the peptide in its natural state when compared to the folding of the heterologous polypeptide of interest in a control plant cell which has only been transformed with the heterologous polypeptide of interest, in the absence of a mammalian chaperone protein.

In yet a further embodiment of the invention co-expression of the heterologous polypeptide of interest and the chaperone protein in the plant cell leads to an at least 1.17-fold increase in the expression of the heterologous polypeptide of interest. It will be appreciated that the increase in expression of the heterologous polypeptide of interest may be an at least 1-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold or an at least 20-fold increase in expression of the heterologous polypeptide of interest.

In a further embodiment of the invention the at least one expression vector includes promoters and/or other regulators, operably linked to the first nucleic acid and to the second nucleic acid.

In a second aspect of the invention there is provided for a plant cell which has been transformed with at least one expression vector, comprising a first nucleic acid encoding a mammalian chaperone protein, and a second nucleic acid encoding a heterologous polypeptide of interest.

In a first embodiment of the invention the mammalian chaperone protein is at least one human chaperone protein selected from the group consisting of calnexin, calreticulin, GRP78/BiP, GRP94, GRP170, HSP47, ERp29, protein disulfide isomerase, peptidyl prolyl cis-trans-isomerase and ERp57. Preferably, the human chaperone protein is selected from calnexin, calreticulin, GRP78/BiP protein disulphide isomerase and/or ERp57.

In a second embodiment the heterologous polypeptide of interest is a glycoprotein. Alternatively, the heterologous polypeptide of interest may be an a non-glycosylated protein.

A third embodiment of the invention provides for expression of the heterologous polypeptide of interest in the plant cell that is increased relative to a control plant cell which has only been transformed with the heterologous polypeptide of interest. Further, the folding of the heterologous polypeptide of interest when co-expressed with the mammalian chaperone protein may be closer to the folding of the peptide in its natural state when compared to the folding of the heterologous polypeptide of interest in a control plant cell which has only been transformed with the heterologous polypeptide of interest, in the absence of a mammalian chaperone protein.

In a further embodiment of this aspect of the invention the invention there is provided for co-expression of the heterologous polypeptide of interest and the chaperone protein in the plant cell which leads to an at least 1.17-fold increase in the expression of the heterologous polypeptide of interest. It will be appreciated that the increase in expression of the heterologous polypeptide of interest may be an at least 1-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold or an at least 20-fold increase in expression of the heterologous polypeptide of interest.

In a further embodiment of the invention the at least one expression vector includes promoters and/or other regulators, operably linked to the first nucleic acid and to the second nucleic acid.

In one embodiment the plant cell may be a plant cell from a monocotyledonous or dicotyledonous plant. Preferably, the plant cell is from a plant selected from the group consisting of maize, rice, sorghum, wheat, cassava, barley, oats, rye, sweet potato, soybean, alfalfa, tobacco, sunflower, cotton, and canola. Most preferably, the plant cell is from a tobacco plant.

In a further aspect of the invention there is provided for a plant comprising the plant cell described in the second aspect of the invention.

BRIEF DESCRIPTION OF THE FIGURES

Non-limiting embodiments of the invention will now be described by way of example only and with reference to the following figures.

SEQUENCE LISTING

Figure 1:
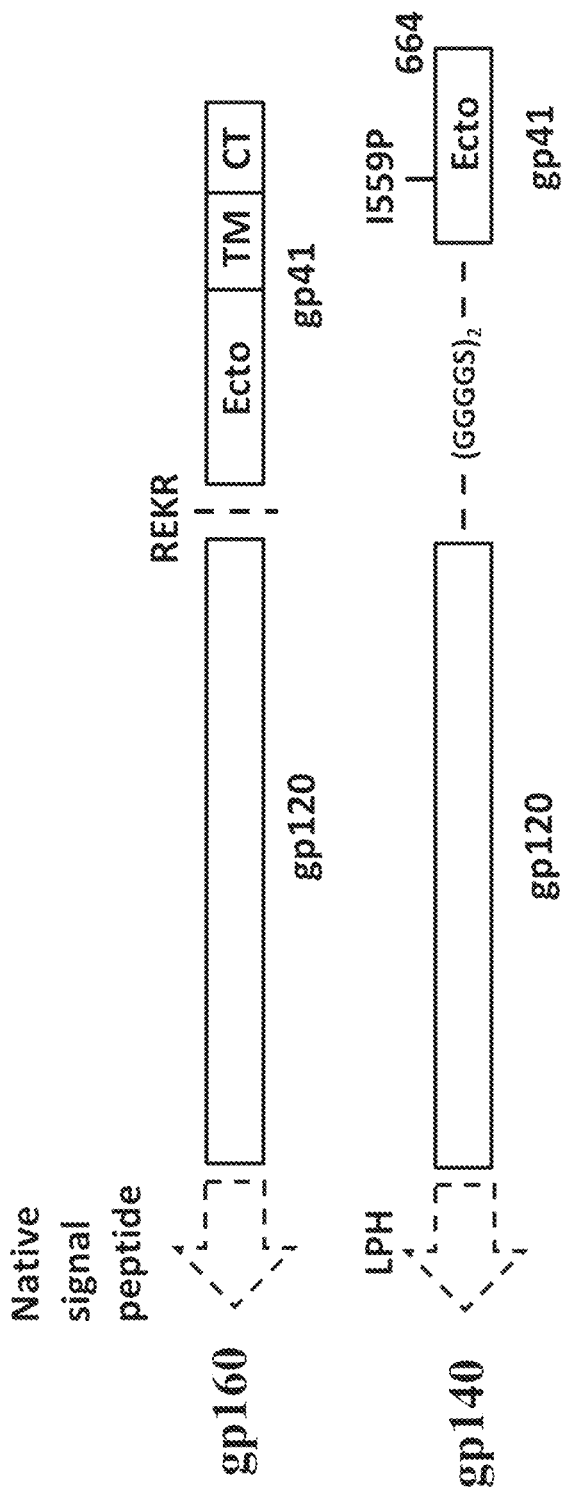
FIG. 1: Schematic of the coding sequences of (A) the native gp160 gene (SEQ ID NO:13) and (B) the gp140 NFL antigen (SEQ ID NO:11). The gp120 and gp41 portions of the proteins are delineated with either the native cleavage sequence (REKR) (SEQ ID NO:21) or flexible (GGGGS)$_2$ linker peptide (SEQ ID NO:22) at the interface of the two subunits. The ectodomain (Ecto), transmembrane (TM) and cytoplasmic (CT) regions of gp41 are indicated. The location of the I559P helix-breaking mutation and amino acid residue 664, where the coding sequence was terminated, is reflected for the gp140 NFL antigen. The native and LPH signal sequences are indicated by the dashed arrows respectively.

The nucleic acid and amino acid sequences listed in the accompanying sequence listing are shown using standard letter abbreviations for nucleotide bases, and the standard three letter abbreviations for amino acids. It will be understood by those of skill in the art that only one strand of each nucleic acid sequence is shown, but that the complementary strand is included by any reference to the displayed strand. In the accompanying sequence listing:
  SEQ ID NO:1—Nucleotide sequence of humanised CRT with restriction sites;
  SEQ ID NO:2—Nucleotide sequence of humanised CNX with restriction sites;
  SEQ ID NO:3—Amino acid sequence of CRT polypeptide;
  SEQ ID NO:4—Amino acid sequence of CNX polypeptide;
  SEQ ID NO:5—Nucleotide sequence of CAP256 SU gp120-HA2;
  SEQ ID NO:6—Amino acid sequence of CAP256 SU gp120-HA2;
  SEQ ID NO:7—Nucleotide sequence of gp41tr fragment;
  SEQ ID NO:8—Amino acid sequence of gp41tr fragment;
  SEQ ID NO:9—Nucleotide sequence of gp120;
  SEQ ID NO:10—Amino acid sequence of gp120;
  SEQ ID NO:11—Nucleotide sequence of CAP256 SU gp140 NFL;
  SEQ ID NO:12—Amino acid sequence of CAP 256 SU gp140 NFL;
  SEQ ID NO:13—Nucleotide sequence of gp160;
  SEQ ID NO:14—Amino acid sequence of gp160;
  SEQ ID NO:15—Nucleotide sequence of gp140;
  SEQ ID NO:16—Amino acid sequence of gp140;
  SEQ ID NO:17—Nucleotide sequence of RFVF LPH-ptGn antigen;
  SEQ ID NO:18—Amino acid sequence of RFVF LPH-ptGn antigen;
  SEQ ID NO:19—Nucleotide sequence of 15-0552 forward primer;
  SEQ ID NO:20—Nucleotide sequence of 15-0553 reverse primer;
  SEQ ID NO:21—Amino acid sequence of the native cleavage sequence; and
  SEQ ID NO:22—Amino acid sequence of the flexible linker peptide.

DETAILED DESCRIPTION OF THE INVENTION

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

The present invention relates to a method for increasing the expression and/or promoting the correct folding of a heterologous polypeptide of interest in a plant cell, comprising co-expressing the heterologous polypeptide of interest with a polypeptide encoding a mammalian chaperone protein, preferably a human chaperone protein. The inventors have surprisingly found that when a mammalian chaperone protein is co-expressed with a heterologous protein of interest that would normally be produced in a mammalian cell line, such as a protein from a mammalian virus, in a plant cell, the expression yields and folding of the heterologous protein are significantly increased. This is in comparison to prior art methods using bacterial chaperones in plant cells or human chaperones in other expression systems. The improved yield and folding observed by the inventors of the present invention is indicated in Table 1 below, which compares the methods known in the art with the method of the present invention. The method of the present invention resulted in an up to 13-fold increase in expression levels and improved the folding of the protein in plants. Given the divergent evolution of plants and mammals, which are estimated to have split from their common ancestor about 1576 million years ago, fundamental differences are expected to exist in the folding machinery of the different expression hosts.

Putative *N. benthamiana* homologues of key human chaperones, known to be involved in glycoprotein synthesis, only have low levels of sequence similarity which may result in incompatibility between a heterologous protein and the endogenous plant chaperones (Table 2). This may account for the low levels of accumulation described for many heterologous glycoproteins in plants (Margolin et al, submitted for publication).

TABLE 1

Summary of notable studies reporting the co-expression of heterologous chaperones for the improved production of recombinant proteins in plants. The differences in relative expression levels are indicated wherever possible.

| Target protein | Chaperone | Chaperone origin | Expression host | Impact | Reference |
|---|---|---|---|---|---|
| HIV-1 gp140 | calreticullin | *H. sapiens* | *N. benthamiana* | ↑13-fold | Present invention |
| HIV-1 gp150 | Calnexin | *H. sapiens* | *N. benthamiana* | ↑1.5-fold | |
| Anti-rabbit IgG | Calnexin | *H. sapiens* | *N. benthamiana* | ↑1.24-fold | |
| RVFV Gn | ERp57 | *H. sapiens* | *N. benthamiana* | ↑2.5-fold | |
| | Calreticulin | *H. sapiens* | *N. benthamiana* | ↑* | |
| HCV E2 (soluble) | Calnexin | *A. thaliana* | *N. benthamiana* | ↑correctly folded protein | US 2014/0127749 A1 |
| HCV E2 (soluble) | Calreticullin | *A. thaliana* | *N. benthamiana* | ↑correctly folded protein | |
| Ebola GP1-H2 fusion | Calreticullin | *A. thaliana* | *N. benthamiana* | ↑Expression | |
| Influenza HA | Calreticullin | *A. thaliana* | *N. benthamiana* | ↑1.2-fold | |
| Influenza HA (soluble) | Calreticullin | *A. thaliana* | *N. benthamiana* | ↑1.6-2.2-fold | |
| Bacterial Tir | CesT | *E. coli* | *N. benthamiana* | ↑ | MacDonald et al 2017 |

HIV = Human Immunodeficiency virus,
RVFV = Rift Valley fever virus,
HCV = Hepatitis C virus,
HSV = Herpes Simplex virus,
GP1-H2 = fusion protein comprising of the Ebola glycoprotein attached to the heavy chain of monoclonal antibody)
*relative increase in production could not be determinded as expression of the protein could not be determined in the absence of co-expressed chaperone.

TABLE 2

Sequence identity of *N. benthamiana* homologues of human molecular chaperones. The sequence identity of homologous plant chaperones were determined by interrogating the *N. benthamiana* genome (V1.0.1) with the amino acid sequences of human chaperones. In each case the sequence was blasted against predicted proteins (blastp) from *N. benthamiana* and the hit with the greatest sequence identity was reflected.

| Chaperone | UniProt accession | Identity (%) |
|---|---|---|
| Calnexin | p27824 | 42.86 |
| Calreticulin | p27797 | 55.68 |
| GRP78 | p11021 | 70.85 |
| ERp57 | p30101 | 34.5 |
| PDI | p07237 | 38.68 |

As used herein the terms "protein," "peptide" or "polypeptide" are used interchangeably and refer to any chain of two or more amino acids, including naturally occurring or non-naturally occurring amino acids or amino acid analogues, irrespective of post-translational modification (e.g., glycosylation or phosphorylation). The amino acids are thus in a polymeric form of any length, linked together by peptide bonds.

The term "heterologous polypeptide of interest" or "polypeptide of interest" as used herein refers to any polypeptide that does not occur naturally in a plant. A heterologous polypeptide of interest may thus include protozoal, bacterial, viral, fungal or animal proteins. The heterologous polypeptide of interest is intended for expression in a plant cell or plant tissue using the methods of the present invention. Non-limiting examples of heterologous polypeptides of interest may include, pharmacological polypeptides (e.g., for medical uses, for cell- and tissue culture) or industrial polypeptides (e.g. enzymes, growth factors) that can be produced according to the methods present invention. The heterologous polypeptides of interest may be useful as vaccines or in vaccines, as well as in other reagents or diagnostics. In particular, the heterologous polypeptide of interest may be a polypeptide from a virus, including Bunyaviruses such as Rift Valley fever virus, Crimean Congo Haemorrhagic fever virus, Flaviviruses such as West Nile virus and Zika virus, Orthomyxoviruses, Togaviruses such as Chikungunya virus, Lentiviruses such as HIV, Herpes viruses such as Epstein Barr virus, Herpes Simplex virus-1, Herpes Simplex virus-2, Filoviruses such as Ebola virus and Marburg virus, Hantaviruses such as Sin Nombre virus, or Henipaviruses such as Nipah virus.

As used herein the term "plant cell which is transformed" refers to a plant or plant cell which has either been stably transformed in order to express a heterologous polypeptide or which has been infiltrated with at least one expression vector which transiently expresses a heterologous polypeptide in the plant or plant cell.

The terms "nucleic acid", "nucleic acid molecule" and "polynucleotide" are used herein interchangeably and encompass both ribonucleotides (RNA) and deoxyribonucleotides (DNA), including cDNA, genomic DNA, and synthetic DNA. The nucleic acid may be double-stranded or single-stranded. Where the nucleic acid is single-stranded, the nucleic acid may be the sense strand or the antisense strand. A nucleic acid molecule may be any chain of two or more covalently bonded nucleotides, including naturally occurring or non-naturally occurring nucleotides, or nucleotide analogs or derivatives. The term "DNA" refers to a sequence of two or more covalently bonded, naturally occurring or modified deoxyribonucleotides.

The term "isolated", is used herein and means having been removed from its natural environment.

The term "purified", relates to the isolation of a molecule or compound in a form that is substantially free of contamination or contaminants. Contaminants are normally associated with the molecule or compound in a natural environment, purified thus means having an increase in purity as a result of being separated from the other components of an original composition. The term "purified nucleic acid" describes a nucleic acid sequence that has been separated from other compounds including, but not limited to, polypeptides, lipids and carbohydrates which it is ordinarily associated with in its natural state.

The term "complementary" refers to two nucleic acids molecules which are capable of forming Watson-Crick base pairs to produce a region of double-strandedness between the two nucleic acid molecules. It will be appreciated by those of skill in the art that each nucleotide in a nucleic acid molecule need not form a matched Watson-Crick base pair with a nucleotide in an opposing complementary strand to form a duplex. One nucleic acid molecule is thus "complementary" to a second nucleic acid molecule if it hybridizes, under conditions of high stringency, with the second nucleic acid molecule. A nucleic acid molecule according to the invention includes both complementary molecules.

As used herein a "substantially identical" sequence is an amino acid or nucleotide sequence that differs from a reference sequence only by one or more conservative substitutions, or by one or more non-conservative substitutions, deletions, or insertions located at positions of the sequence that do not destroy or substantially reduce the antigenicity of one or more of the expressed polypeptides or of the polypeptides encoded by the nucleic acid molecules. Alignment for purposes of determining percent sequence identity can be achieved in various ways that are within the knowledge of those with skill in the art. These include using, for instance, computer software such as ALIGN, Megalign (DNASTAR), CLUSTALW or BLAST software. Those skilled in the art can readily determine appropriate parameters for measuring alignment, including any algorithms needed to achieve maximal alignment over the full length of the sequences being compared. In one embodiment of the invention there is provided for a polypeptide or polynucleotide sequence that has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or 100% sequence identity to the sequences described herein.

Alternatively, or additionally, two nucleic acid sequences may be "substantially identical" if they hybridize under high stringency conditions. The "stringency" of a hybridisation reaction is readily determinable by one of ordinary skill in the art, and generally is an empirical calculation which depends upon probe length, washing temperature, and salt concentration. In general, longer probes required higher temperatures for proper annealing, while shorter probes require lower temperatures. Hybridisation generally depends on the ability of denatured DNA to re-anneal when complementary strands are present in an environment below their melting temperature. A typical example of such "stringent" hybridisation conditions would be hybridisation carried out for 18 hours at 65° C. with gentle shaking, a first wash for 12 min at 65° C. in Wash Buffer A (0.5% SDS; 2×SSC), and a second wash for 10 min at 65° C. in Wash Buffer B (0.1% SDS; 0.5% SSC).

Those skilled in the art will appreciate that polypeptides, peptides or peptide analogues can be synthesised using standard chemical techniques, for instance, by automated synthesis using solution or solid phase synthesis methodology. Automated peptide synthesisers are commercially available and use techniques known in the art. Polypeptides, peptides and peptide analogues can also be prepared from their corresponding nucleic acid molecules using recombinant DNA technology.

As used herein, the term "gene" refers to a nucleic acid that encodes a functional product, for instance a RNA, polypeptide or protein. A gene may include regulatory sequences upstream or downstream of the sequence encoding the functional product.

As used herein, the term "coding sequence" refers to a nucleic acid sequence that encodes a specific amino acid sequence. On the other hand a "regulatory sequence" refers to a nucleotide sequence located either upstream, downstream or within a coding sequence. Generally regulatory sequences influence the transcription, RNA processing or stability, or translation of an associated coding sequence. Regulatory sequences include but are not limited to: effector binding sites, enhancers, introns, polyadenylation recognition sequences, promoters, RNA processing sites, stem-loop structures, translation leader sequences and the like.

The term "chaperone" refers to polypeptides which facilitate protein folding by non-enzymatic means, in that they do not catalyse the chemical modification of any structures in folding polypeptides. Chaperones potentiate the correct folding of polypeptides by facilitating correct structural alignment thereof. Molecular chaperones are well known in the art and several families thereof have previously been characterised. It is envisioned that for the purposes of the present invention any molecular chaperone protein will be suitable for use, including chaperone proteins derived from a host organism best suited to the expression of a heterologous protein of interest. In one embodiment the chaperone protein includes cytoplasmic chaperones, cytosolic chaperones or endoplasmic reticulum chaperones from other plants, animals, insects, humans, yeast or fungi. In an alternative embodiment the chaperone protein is a mammalian chaperone protein, preferably a human chaperone protein, selected from the group consisting of general chaperones, lectin chaperones, and non-classical chaperones. The term chaperone includes molecular chaperones selected from the following non-exhaustive group: calnexin, calreticulin, GRP78/BiP, GRP94, GRP170, HSP47, ERp29, Protein disulfide isomerase (PDI), peptidyl prolyl cis-trans-isomerase (PPI), and ERp57. Further, the chaperones may be expressed in combinations or co-expressed with oligosaccaryltransferases to improve the glycosylation. For example Leishmania major LmSTT3D may be co-expressed with calreticulin, to improve the glycan occupancy of the recombinant HIV-1 gp140 Env proteins or other glycoproteins.

As used herein, the term "glycoprotein" refers to a glycoprotein that would normally be produced in a mammalian cell, including viral glycoproteins or viruses having a mammalian host, and antibodies.

In some embodiments, the genes used in the method of the invention may be operably linked to other sequences. By "operably linked" is meant that the nucleic acid molecules encoding the recombinant polypeptides of the invention and regulatory sequences are connected in such a way as to permit expression of the proteins when the appropriate molecules are bound to the regulatory sequences. Such operably linked sequences may be contained in vectors or expression constructs which can be transformed or transfected into host cells for expression. It will be appreciated that any vector or vectors can be used for the purposes of expressing the recombinant antigenic polypeptides of the invention.

The term "promoter" refers to a DNA sequence that is capable of controlling the expression of a nucleic acid coding sequence or functional RNA. A promoter may be based entirely on a native gene or it may be comprised of different elements from different promoters found in nature. Different promoters are capable of directing the expression of a gene in different cell types, or at different stages of development, or in response to different environmental or physiological conditions. A "constitutive promoter" is a promoter that direct the expression of a gene of interest in most host cell types most of the time.

The term "recombinant" means that something has been recombined. When used with reference to a nucleic acid construct the term refers to a molecule that comprises nucleic acid sequences that are joined together or produced by means of molecular biological techniques. The term "recombinant" when used in reference to a protein or a polypeptide refers to a protein or polypeptide molecule which is expressed from a recombinant nucleic acid construct created by means of molecular biological techniques. Recombinant nucleic acid constructs may include a nucleotide sequence which is ligated to, or is manipulated to become ligated to, a nucleic acid sequence to which it is not ligated in nature, or to which it is ligated at a different location in nature. Accordingly, a recombinant nucleic acid construct indicates that the nucleic acid molecule has been manipulated using genetic engineering, i.e. by human intervention. Recombinant nucleic acid constructs may be introduced into a host cell by transformation. Such recombinant nucleic acid constructs may include sequences derived from the same host cell species or from different host cell species.

The term "vector" refers to a means by which polynucleotides or gene sequences can be introduced into a cell. There are various types of vectors known in the art including plasmids, viruses, bacteriophages and cosmids. Generally polynucleotides or gene sequences are introduced into a vector by means of a cassette. The term "cassette" refers to a polynucleotide or gene sequence that is expressed from a vector, for example, the polynucleotide or gene sequences encoding the acyl transferase polypeptides of the invention. A cassette generally comprises a gene sequence inserted into a vector, which in some embodiments, provides regulatory sequences for expressing the polynucleotide or gene sequences. In other embodiments, the vector provides the regulatory sequences for the expression of the acyl transferase polypeptides. In further embodiments, the vector provides some regulatory sequences and the nucleotide or gene sequence provides other regulatory sequences. "Regulatory sequences" include but are not limited to promoters, transcription termination sequences, enhancers, splice acceptors, donor sequences, introns, ribosome binding sequences, poly(A) addition sequences, and/or origins of replication.

The following examples are offered by way of illustration and not by way of limitation.

Example 1

Gene Design and Cloning into pEAQ-HT

Construction of pEAQ-HT Expression Plasmids Encoding a Soluble HIV Envelope Gp140 NFL Antigen A soluble gp140 antigen was designed from the CAP256 SU viral isolate based on the NFL design described by Sharma et al., 2015 (SEQ ID NO:12). This approach obviates the need for furin-mediated proteolytic cleavage which does not occur naturally in planta (Wilbers et al., 2016). The native HIV envelope cleavage site was replaced with a 10 amino acid flexible linker comprising of 2 repeats of the glycine-serine based (GGGGS) motif. The isoleucine at residue 559 in the N-terminal heptad repeat of gp41 was mutated to a proline and the coding sequence prematurely terminated by the introduction of a stop codon after amino acid residue 664. The gene coding sequences were optimized to reflect the preferred human codon usage and Age1 and Xho1 restriction sites added to the 5' and 3' terminal ends of the genes respectively. A synthetic Not1 site was included prior to the stop codon resulting in a run of 3 alanine residues at the C terminal end of the protein. Lastly, the native signal sequence was replaced with the murine mAB24 heavy chain-derived LPH signal peptide, to direct translocation of the recombinant protein through the plant secretory pathway (FIG. 1) (SEQ ID NO:11).

The coding sequence of the full length envelope from the HIV CAP256 SU virus (clone 256.2.06.c7) was provided by Dr Penny Moore (Senior Medical Scientist, Centre for HIV and STIs, National Institute for Communicable Diseases, Johannesburg) (SEQ ID NO:13). The coding sequence was designed as 2 separate fragments that needed to be assembled. The first fragment encoded the gp120 region of the envelope protein followed by a flexible linker peptide and contained an Age1 restriction enzyme recognition site at the 5' end and a BamH1 at the 3' end. The truncated gp41 fragment contained a 5' BamH1 and a 3' terminal Xho1 recognition site to enable the in-frame assembly of the 2 fragments. The genes were synthesized by GenScript and provided as recombinant plasmid constructs with the fragments cloned into the pUC57 expression plasmid.

The gp120-HA2 fragment (SEQ ID NO:5) was contained in the pUC57: CAP256 SU gp120-HA2 plasmid, assembled in an independent study, was provided by Michiel van Diepen (Principle Scientific Officer, Department of Pathology, University of Cape Town). The gp41tr fragment (SEQ ID NO:7) was received as the original pUC57 clone from GenScript. The pUC57:gp120-HA2 clone was digested with BamH1 and Xho1 to remove the HA2 fragment and enable the gp41tr coding sequence to be inserted at the C terminal end of the gp120 linker. Similarly, the pUC57:gp41tr clone was digested with BamH1 and Xho1 to liberate the gp41tr insert from the pUC57 vector backbone. The restriction products were resolved on a 0.8% gel and the fragments corresponding to pUC57 vector backbone (containing the gp120 coding sequence) and the gp41 fragment recovered using the Zymogen™ Gel DNA recovery kit. The insert was ligated into the pUC57:gp120 backbone using Fermentas T4 DNA ligase, as per the manufacturer's instructions, to yield the CAP256 SU gp140 NFL gene (SEQ ID NO:11) and the reaction thermally inactivated at 65° C. for 10 minutes.

The products of the ligation reaction were transformed into E. cloni 10G Chemically Competent Cells (Lucigen) as per the manufacturer's instructions. Putative clones were cultured overnight in 1 ml of LB broth and each culture was subjected to a small scale DNA isolation. The resulting plasmid DNA was screened by restriction enzyme digestion using Age1, BamH1 and Xho1 and the restriction fragments resolved by electrophoresis on an agarose gel. One of the positive clones was cultured in 100 ml LB and subjected to a large scale DNA isolation to obtain working stocks of the plasmid.

Following assembly of the HIV gp140 NFL genes in pUC57 it was shotgun cloned into the pEAQ-HT expression plasmid. The gp140 NFL coding sequences was excised from the pUC57 vector backbones using Age1 and Xho1. Similarly the pEAQ-HT expression vector was digested with Age1 and Xho1 to generate compatible sticky ends for cloning. The restriction enzymes were heat inactivated at 80° C., for 5 minutes, and the gp140 genes ligated into pEAQ-HT, using a 3:1 ratio of insert to vector. The ligation reaction was terminated by thermal inactivation of the enzyme and the ligation products transformed into E. cloni 10G Chemically Competent Cells (Lucigen).

Figure 2:
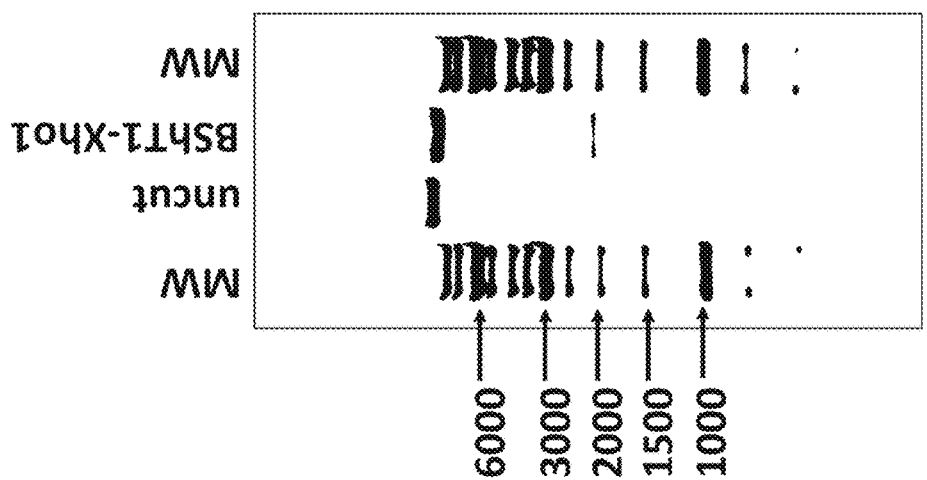
FIG. 2: Restriction analysis of recombinant pEAQ-HT expression vectors encoding the CAP256 SU gp140 NFL antigens. (A) shows the restriction fragments yielded by digestion of pEAQ-HT: CAP256 SU gp140 NFL. The corresponding vector maps for the constructs are shown alongside in (B).
Figure 2:
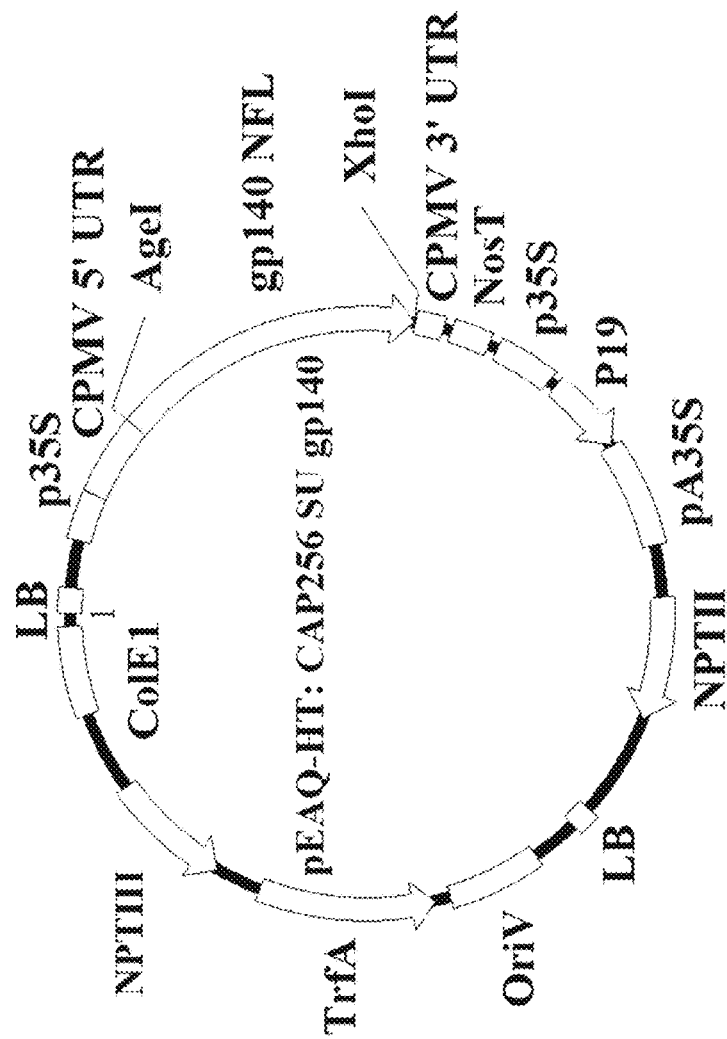

Putative transformants were screened by colony PCR using the 15-0552 and 15-0553 primers (Table 3). The genetic integrity of the final clone was verified by restriction analysis using the Age1 and Xho1 enzymes that flank the insert (FIG. 2) and sequencing across the cloning junctions with vector-specific primers 15-0552 and 15-0553 primers (Table 3).

tion digestion with Age1 and Xho1. The pEAQ-HT expression vector was similarly digested with both enzymes to generate compatible sticky ends. The resulting restriction

TABLE 3

Primers used for screening putative A. tumefaciens AGL1 transformants.

| Primer | Orientation | Function | Sequence (5'-3') | SEQ ID NO: |
|---|---|---|---|---|
| 15-0552 | Forward | Sequencing of recombinant pEAQ-HT, screening of putative clones | TTCTTCTTCTTGCTGATTGG | SEQ ID NO: 19 |
| 15-0553 | Reverse | Sequencing of recombinant pEAQ-HT, screening of putative clones | CACAGAAAACCGCTCACC | SEQ ID NO: 20 |

The expected product of 2000 bp was liberated from the vector backbone by restriction digestion and agarose gel electrophoresis (FIG. 2A).

The expression vectors were transformed into *A. tumefaciens* AGL1 and putative transformants verified by PCR screening of bacteria-derived plasmid DNA after in vitro culturing (data not shown).

Aliquots of 400 ng of recombinant plasmid DNA were mixed with 100 µl of cells, in a 0.1 cm gap electroporation curvette (Molecular BioProducts), and electroporated in accordance with Maclean et al., 2007. Transformants were selected on Luria agar plates, supplemented with 50 µg/ml carbenicillin (Sigma-Adrich) and 30 µg/ml kanamycin (Sigma-Aldrich). Putative recombinant colonies were propagated in liquid broth and subjected to a small scale crude DNA isolation. A 5 µl aliquot of the crude plasmid DNA was screened directly by PCR, using the 15-0552 (SEQ ID NO:19) and 15-0553 (SEQ ID NO:20) primers, at an annealing temperature of 65° C. PCR screening was performed using ImmoMix™ Red (Bioline) in accordance with the manufacturer's instructions. Once successful transformants had been identified, recombinant strains were cultured in LB media and stored at −80° C. as 25% glycerol stocks.

Construction of pEAQ-HT Expression Plasmids Encoding Molecular Chaperones

Design of Chaperone Gene Coding Sequences

The amino acid sequences for human calnexin (CNX) (SEQ ID NO:4) and human calreticulin (CRT) (SEQ ID NO:3) were retrieved from the UniProt database (accession numbers P27824 and P27797 respectively) and optimized to reflect the preferred human codon usage. No additional signal sequences were added to either the CNX (SEQ ID NO:2) or CRT (SEQ ID NO:1) genes to enable their natural localization to the ER membrane and ER lumen respectively, as required for their role in protein folding. Synthetic Age1 and Xho1 restriction enzyme sites were incorporated at the 5' and 3' terminal ends of the gene coding sequences respectively, to facilitate cloning into the pEAQ-HT expression vector. The genes were synthesized by GenScript and received as recombinant plasmids that were generated by cloning the DNA sequences into the pUC57 cloning vector.

Sub-Cloning of the Gene Coding Sequences into pEAQ-HT Expression Vector

Figure 3:
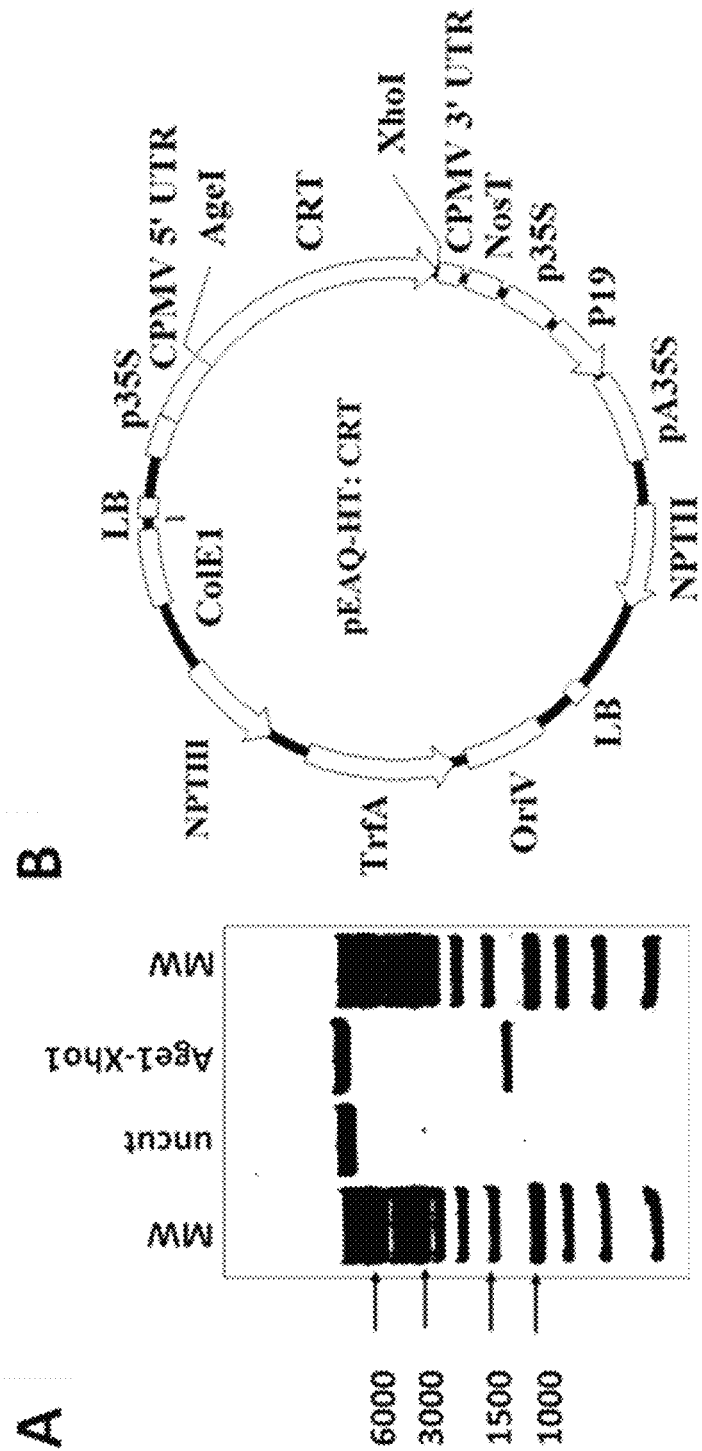
FIG. 3: Restriction analysis to verify the genetic integrity of recombinant pEAQ-HT expression constructs encoding human molecular chaperones. (A) and (C) show the restriction fragments yielded by digestion of pEAQ-HT: CRT and pEAQ-HT: CNX respectively. The corresponding vector maps for the constructs are shown alongside in (B) and (D).

The CRT (SEQ ID NO:1) and CNX (SEQ ID NO:2) genes were excised from the pUC57 plasmid backbone by restricfragments were resolved by electrophoresis on a 0.8% agarose gel and both the vector backbone and gene coding sequences recovered under blue light with a scalpel. The DNA was purified from contaminating agarose and the genes ligated into the pEAQ-HT vector backbone using a 3:1 ratio of insert to vector. The reaction was terminated by thermal inactivation and the ligation products transformed into *E. cloni* 10 G Chemically Competent Cells (Lucigen). Transformants were selected on Luria agar supplemented with 50 µg/ml kanamycin. Putative clones were cultivated in 1 ml of LB media and subjected to a small scale DNA isolation. Plasmid DNA was screened with Age1 and Xho1 restriction enzymes to liberate the gene from the pEAQ-HT plasmid backbone. The genetic integrity of the final clone was verified by restriction analysis and sequencing as described above. Restriction enzyme digestion with Age1 and Xho1 liberated fragments of 1260 bp and 1785 bp corresponding to the CRT and CNX coding sequences respectively (FIG. 3A and FIG. 3C). The plasmids were then electroporated into *A. tumefaciens* AGL1 and putative transformants screened by PCR of bacterial-derived DNA (data not shown).

Example 2

Transient Co-Expression of Recombinant CAP256 SU gp140 NFL and Human Chaperones in Planta Glycerol stocks of recombinant *A. tumefaciens* AGL1 were revived in 10 ml LB media, supplemented with 50 µg/ml carbenicillin (Sigma-Aldrich) and 50 µg/ml kanamycin (Sigma-Aldrich). The cultures were sequentially scaled up to 1.25 litres in LBB media, with 20 µM acetosyringone supplemented during the final culture step. The bacterial suspension was then adjusted to an $OD_{600}$ of 2.0, using freshly prepared Resuspension Media (10 mM MgCl2, 10 mM MES [pH5.6], 200 µM acetosyringone). Equal volumes of cultures expressing CRT (SEQ ID NO:3) or CNX (SEQ ID NO:4) were mixed with recombinant *A. tumefaciens* encoding CAP256 SU gp140 NFL (SEQ ID NO:12) resulting in a final $OD_{600}$ of 1 for each strain. Control cultures expressing only a single protein were also adjusted to a final $OD_{600}$ of 1. Whole *Nicotiana benthamiana* plants were submerged, upside down, in a beaker of the bacterial culture placed inside a vacuum chamber. A vacuum of −80 kilopascal was applied to the chamber and the procedure repeated 2-3 times to ensure complete infiltration of the leaves. The agroinfiltrated plants were then returned to the greenhouse and incubated under the same environmental conditions until harvest.

Small-scale comparisons of protein expression were conducted on crude leaf homogenate derived from 3 plants per construct to account for biological variability. Six leaf clippings were harvested from each plant (2 clippings per leaf, 3 leaves per plant) weighed, and consequently finely ground in liquid nitrogen. The plant material was then resuspended in 3 buffer volumes of PBS supplemented with cOmplete™ EDTA-free protease inhibitor (Roche). The plant slurries were incubated at 4° C., for 1 hour, with gentle agitation and then clarified by centrifugation at 14 000 rpm for 15 minutes. The supernatant was retained and stored at −20° C. In some cases, following centrifugation, the insoluble plant debris was retained for samples containing CNX.

Western blotting of crude leaf extract was used to compare the relative expression levels of the antigen in the presence and absence of each of the chaperones. Equal amounts of total soluble protein were resolved on SDS-PAGE gel to allow for comparisons to be made. Following transfer the membranes were blocked with 5% milk powder in PBS. Alternatively, for western blots to detect Env, 2% BSA was used instead of milk as a blocking agent. Recombinant CRT and CNX were detected using 1:5000 dilutions of polyclonal rabbit anti-calreticulin (Abcam, ab2907) and rabbit polyclonal anti-calnexin (Abcam, ab75081) respectively. In turn, the primary antibodies were detected with 1:10 000 anti-rabbit IgG-alkaline phosphatase (Sigma, A3687). The pellet samples were solubilized in 2 buffer volumes of 4×SDS-PAGE loading dye and processed for western blotting. Recombinant Envelope was detected with 1:1000 dilution of goat anti-HIV-1 gp120 antibody (AbD Serotec) overnight, at 4° C. The primary antibody was detected with 1:10 000 dilution of GT34 anti-sheep/goat secondary antibody (Sigma-Aldrich).

Figure 4:
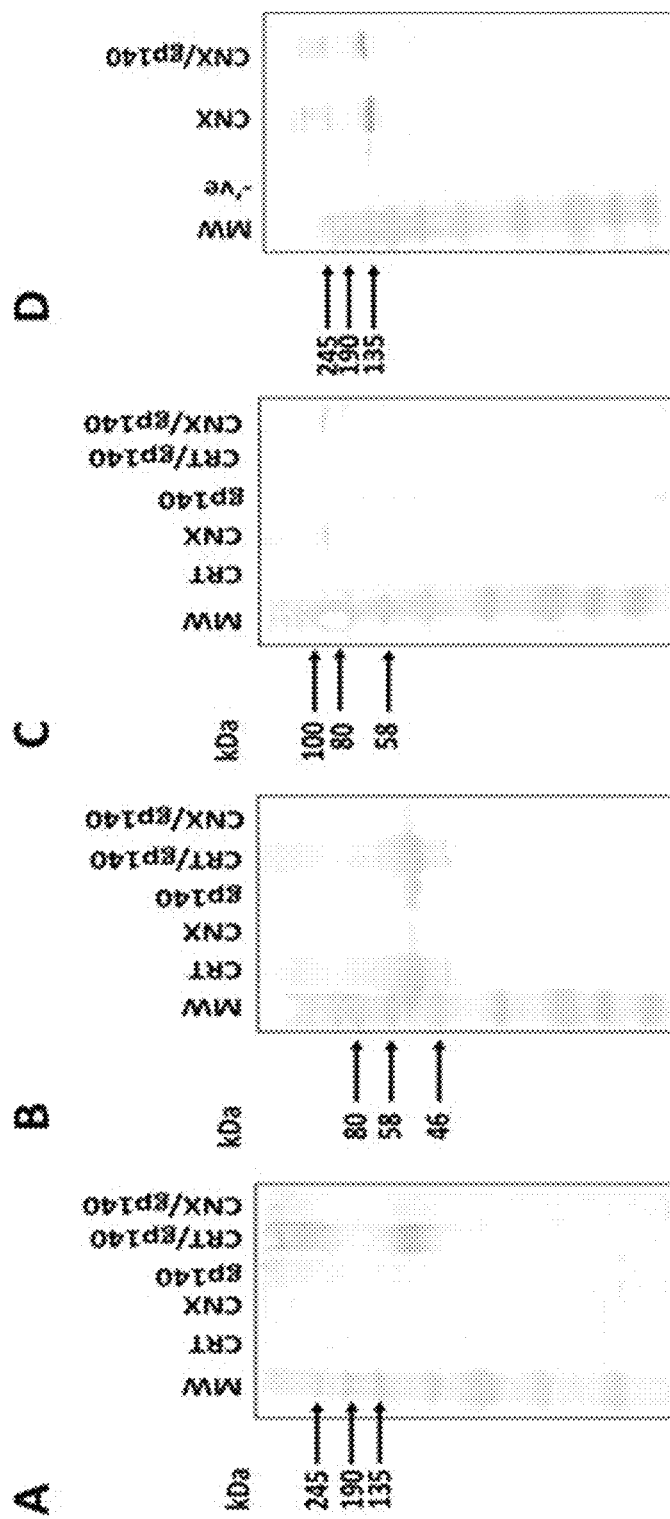
FIG. 4: Western blotting to detect expression of recombinant (A) CAP256 SU gp140 NFL (B) calreticulin (CRT) and (C) and (D) calnexin (CNX) in crude leaf extracts. Crude TSP was loaded in western blots (A)-(C). Solubilized pellet samples were loaded in (D).

Co-expression of calreticulin resulted in a marked increase in CAP256 SU gp140 NFL expression, whereas co-expression of calnexin did not lead to any easily discernible change based on initial western blots (FIG. 4A). This clearly highlights the profound increase in CAP256 SU gp140 NFL expression resulting from heterologous calreticulin production in situ. Expression of both calreticulin and calnexin were confirmed in the presence and absence of co-expressed CAP256 SU gp140 NFL (FIG. 4B and FIG. 4C respectively). Calreticulin expression was also detected in samples where the recombinant chaperone was not expressed, possibly due to the presence of low levels of endogenous calreticulin in plants. Interestingly, the calreticulin background signal appeared greater when CAP256 SU gp140 was expressed, suggesting that it may play an important role in the folding of the glycoprotein. The low intensity of the calnexin signal observed in the soluble protein fraction is most likely due to retention of the protein in the insoluble fraction during purification. This was confirmed by western blotting of solubilized plant pellets after expression (FIG. 4D).

Figure 5:
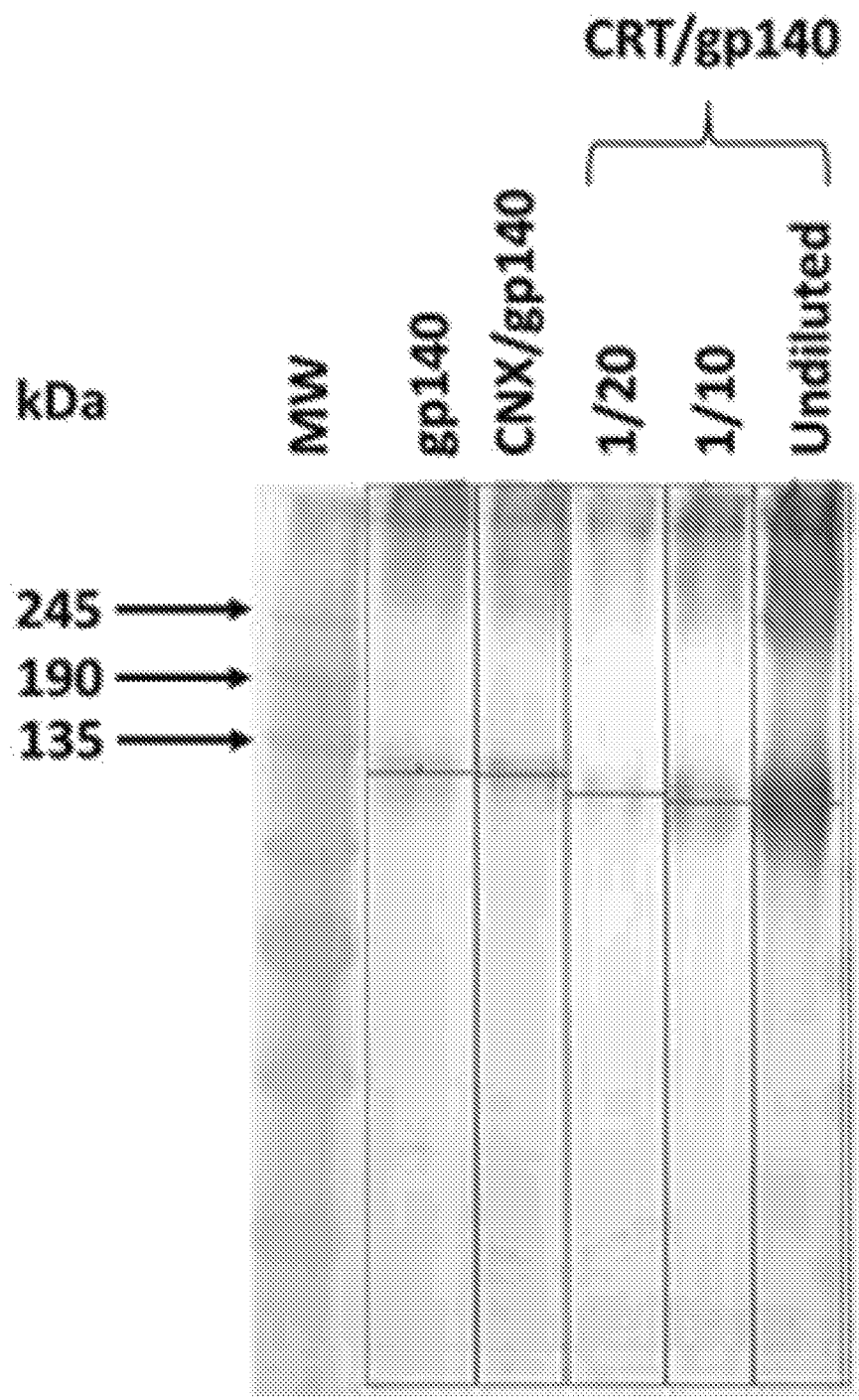
FIG. 5: Representative western blot used to determine relative Envelope glycoprotein expression levels in the presence of calreticulin (CRT) and calnexin (CNX) by gel densitometry.

The relative levels of envelope expression were quantified based on band intensity, by gel densitometry, following western blotting. Following quantification, equal amounts of crude total soluble protein were resolved by SDS-PAGE. In the case of samples containing high levels of recombinant gp140 NFL, a dilution series was included (FIG. 5). Images were captured using the BioRad Molecular Imager® Gel Doc™ XR+ System and analysed using Image Lab™ Software (V5.2.1). Individual lanes were defined manually and the software protocol run for low intensity bands. Saturated bands were excluded for quantification. The relative expression levels were adjusted for the dilution factor where necessary. Results were presented as the mean of 3 independent infiltration experiments. The co-expression of calreticulin increased the levels of heterologous Envelope expression by 12.7-fold whereas calnexin marginally increased Envelope expression by 1.17-fold.

Example 3

Influence of Human Calreticulin and Calnexin Expression in Planta on the Accumulation of a Soluble Rift Valley Fever Virus (RVFV)

The development of a plant-produced RVFV vaccine has potential as a cheap way of providing immune-mediated protection against the virus. Expression of glycoprotein antigens from RVFV in plants however has proved challenging and only a soluble Gn antigen (SEQ ID NO:18) has been successfully expressed, albeit at low levels. A glycerol stock of recombinant A. tumefaciens LBA4044 (pEAQ-HT-LPH-ptGn) was obtained from the Biopharming Research Unit culture collection (#1753). The antigen has been modified by truncating the coding sequence to eliminate the transmembrane and cytoplasmic regions and by substituting the native signal peptide for the LPH murine monoclonal antibody signal peptide. It is known that the presence of a transmembrane domain on a glycoprotein makes it much harder to express in plants. Additionally the coding sequence has been optimized to reflect the preferred codon usage for plants (SEQ ID NO:17) (Sandiswa Mbewana, PhD thesis).

Figure 6:
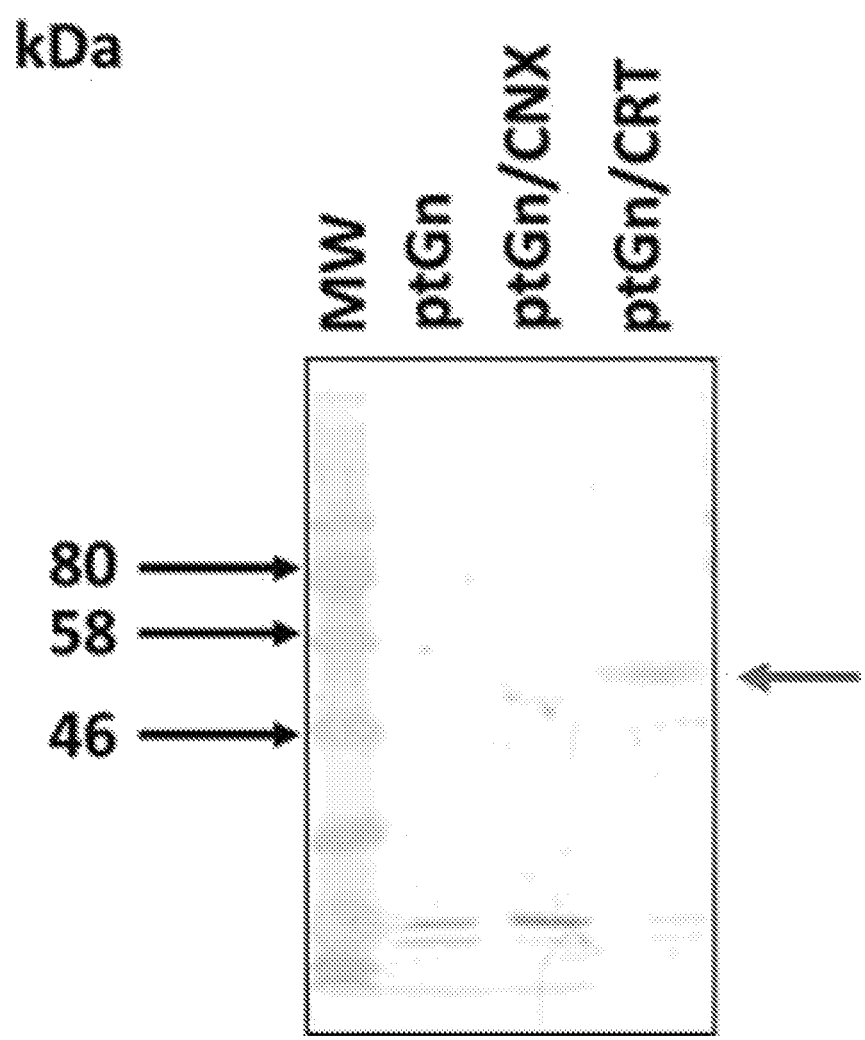
FIG. 6: Western blot to detect expression of recombinant ptGn in planta.

A glycerol stock of the recombinant A. tumefaciens strain was scaled up to 1.25 litres in LBB media supplemented with 30 µg kanamycin, 50 µg rifampicin and 2 mM $MgSO_4$. Rifampicin was omitted during the final culture step and the media was supplemented with 20 µM acetosyringone. Similarly, glycerol stocks of recombinant A. tumefaciens encoding CRT or CNX were scaled up to 1.25 litres as described in Example 2. The bacterial suspension of the cultures encoding the chaperones was adjusted as indicated in Example 2. In contrast the culture encoding RVFV ptGn was adjusted to 0.5. Equal volumes of cultures expressing the glycoprotein and each chaperone were mixed. Similarly, a control culture was prepared comprising of A. tumefaciens LBA4044 (pEAQ-HT-LPH-ptGn) diluted to an $OD_{600}$ of 0.25 which was previously determined to enable optimal accumulation of the glycoprotein. Groups of 3 N. benthamiana plants were infiltrated with each recombinant culture and protein harvested with 100 mM Tris/HCl[pH7.5] and subjected to western blotting on a 10% gel as outlined in Example 2. Expression of the recombinant glycoprotein was detected as described in Example 2 but using with 1:500 dilution of polyclonal rabbit antibodies raised against a synthetic peptide from the Gn glycoprotein from an independent study. Expression of the recombinant glycoprotein (49 kDa) was only detectable in the presence of co-expressed calreticulin (FIG. 6).

Example 4

Human Calnexin Improves the Expression Yields of a Membrane Bound HIV Envelope Glycoprotein Whilst calreticulin preferentially interacts with proteins located in the ER lumen, calnexin (its membrane-bound homologue) plays a more prominent role in the folding of proteins associating with the ER-membrane. A near full length HIV antigen was designed based on the CAP256 SU Envelope. The sequence was modified to reflect the optimum human codon usage and the native signal peptide was replaced with the murine monoclonal antibody derived LPH signal peptide for expression in planta. The sequence was also truncated, to gp150, as previously described by Burgers et al (2006) to improve expression levels.

Figure 7:
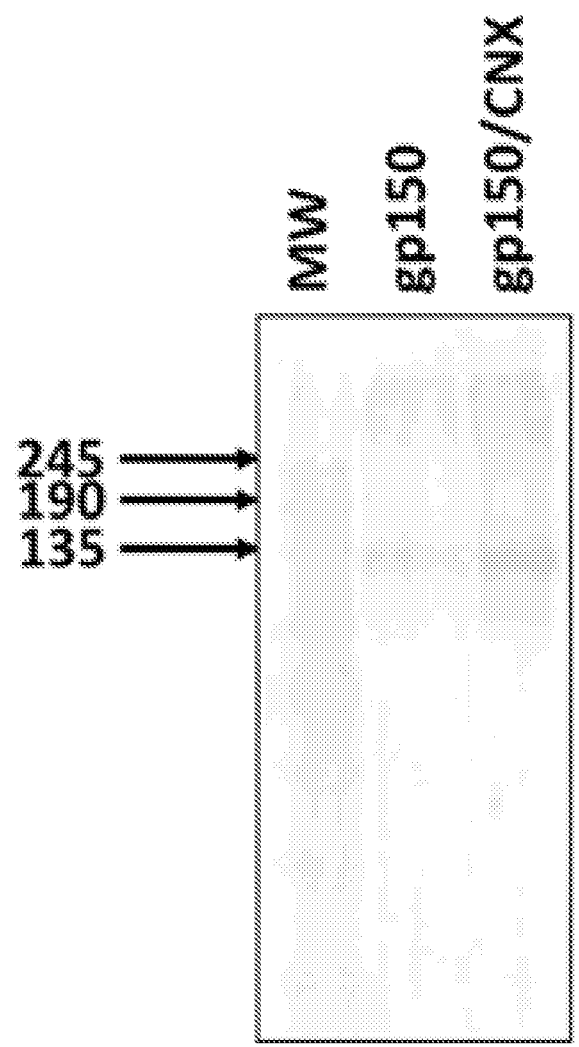
FIG. 7: Western blot to determine the influence of calnexin (CNX) on HIV Env gp150 expression in plants.

Recombinant *A. tumefaciens* encoding the viral glycoprotein and human molecular chaperone were cultivated in LBB media supplemented with 50 μg/ml Kanamycin and 25 μg/ml carbenicillin. The culture media was further supplemented with 20 μM acetosyringone in the final culture step. The bacterial culture densities ($OD_{600}$) were adjusted and the 2 cultures mixed to give a final $OD_{600}$ of 0.5 for each strain. Groups of 3 plants were infiltrated as described in examples 2 and 3. Leaf material was harvest 5 days post infiltration in PBS and equal amounts of total soluble protein analysed by western blotting as described in Example 2 (FIG. 7). Co-expression of human CNX resulted in a 1.5-fold increase in relative expression of the protein.

Example 5

Human Calnexin Improves the Expression Yields of a Membrane Bound HIV Envelope Glycoprotein Co-Expressed with HIV Gag for Production of Virus-Like Particles In another embodiment of this invention gp150 may be expressed alone, or in the presence of HIV Gag for the production of a virus-like particle presenting HIV Env. The Gag antigen may be a naturally occurring protein isolated from a virus or a synthetic antigen designed in silico. In this example a Gag subtype C mosaic antigen previously designed in silico, to maximize the coverage of potential T cell epitopes was used. The Env gp150 sequence was further modified to replace the native cleavage sequence with a glycine-rich linker peptide $(GGGGS)_2$ (SEQ ID NO:22) to circumvent the need for furin-mediated cleavage which does not occur in plants.

Figure 8:
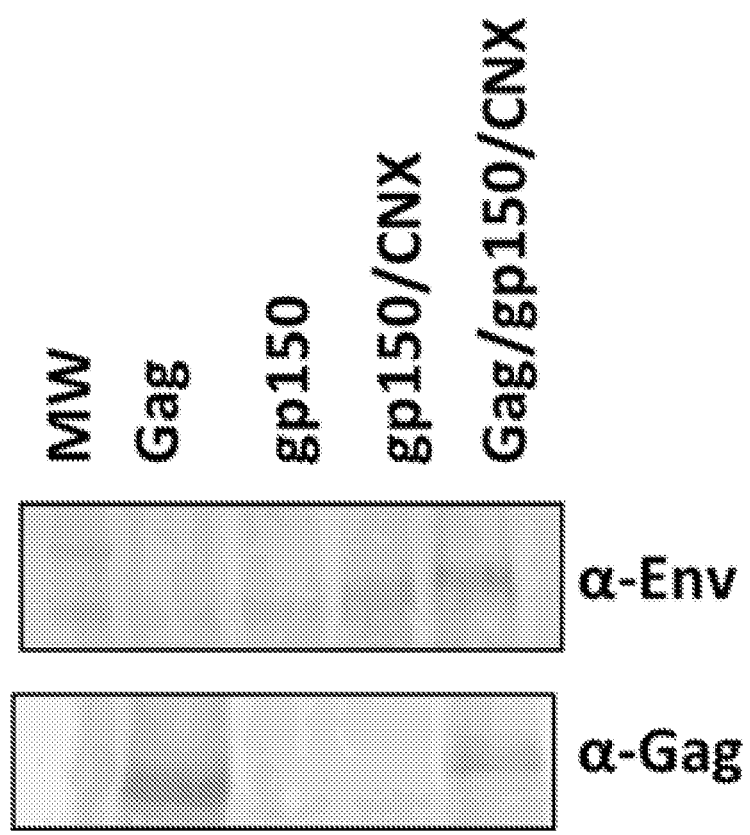
FIG. 8: Western blot to verify the successful co-expression of HIV-1 Gag with calnexin (CNX) and HIV Env gp150 in plants.

Recombinant *A. tumefaciens* clones were scaled up as described in Example 4. The culture densities ($OD_{600}$) were adjusted and pooled to result in equal amounts of each strain in the final inoculum. Groups of 3 plants were infiltrated and crude protein recovered as described in Example 2. Expression of the recombinant proteins was verified by western blotting (FIG. 8). HIV Env was detected as outlined in Example 2. Recombinant Gag was detected using a polyclonal goat anti-Gag antibody which in turn was detected using a 1:10 000 anti-goat/sheep secondary antibody. FIG. 8 shows that chaperones and a glycoprotein can be co-expressed with a structural protein for the generation of a virus-like particle.

Example 6

Figure 9:
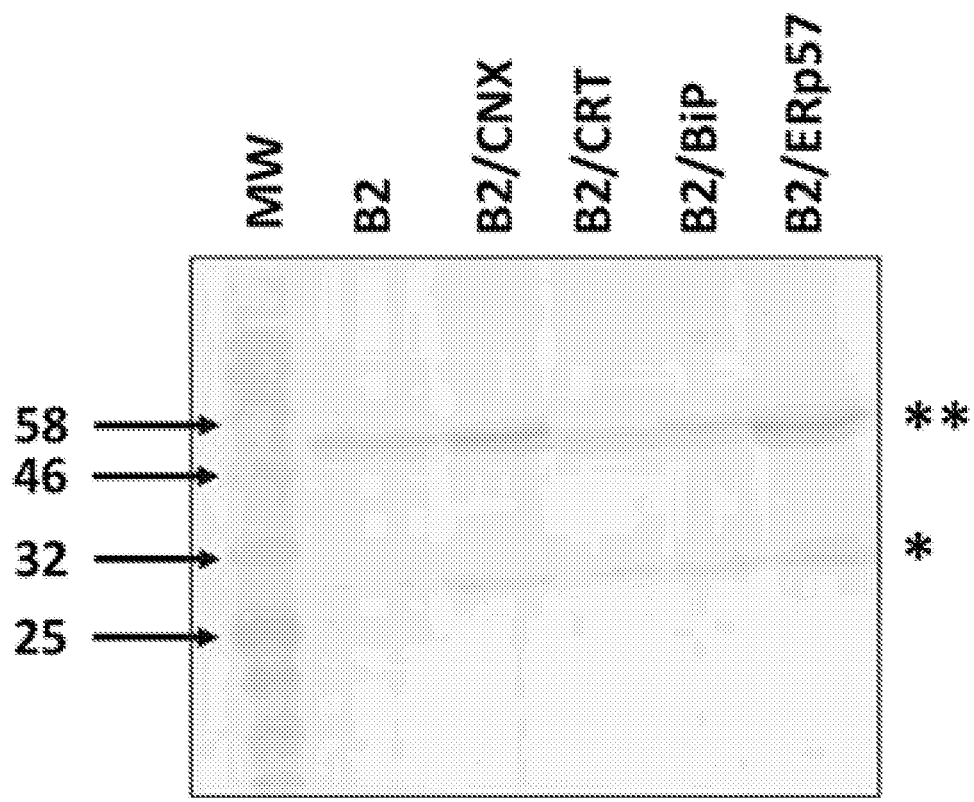
FIG. 9: Western blot to determine relative expression of B2 monoclonal antibody in the presence and absence of co-expressed human molecular chaperones. **=antibody heavy chain; *=antibody light chain

Co-Expression of Human Molecular Chaperones with a Prototype Monoclonal Antibody In recent years plant molecular farming has shown particular promise for the production of recombinant antibodies. However, low expression yields remain a challenge and strategies to improve production levels are critical for industrial manufacture. Thus, a glycerol stock of recombinant *A. tumefaciens* encoding a humanized anti-rabbit antibody (B2) was obtained from the BRU culture collection. This construct expresses an anti-rabbit single chain variable fragment cloned into human IgG backbone. Recombinant *A. tumefaciens* strains encoding the antibody and human chaperone proteins were scaled up as described in Example 2 and equal amounts of bacteria expressing each chaperone were co-infiltrated with bacteria expressing the B2 monoclonal antibody. Two additional chaperones were also used, namely BiP/GRP78 (UniProt accession number: P11021), which has been shown to associate with recombinant antibodies in plants, and ERp57 (UniProt accession number: P30101) which associates with CNX/CRT to mediate disulphide bonding. Crude leaf lysate was harvested 5 days post agroinfiltration, quantified and analysed by western blotting. The recombinant antibody was detected directly using 1:5000 anti-human IgG H+L alkaline phosphatase conjugate (Promega). Relative expression levels were determined as indicated in example 2, based on the heavy chain signal. ERp57 increased the relative expression by 2.5 fold whereas CNX improved relative expression by 1.24-fold (FIG. 9).

This demonstrates that the co-expression of chaperones is not limited to viral glycoproteins and may likely work for other heterologous glycoproteins. Furthermore, this may also not be limited to glycoproteins. Non-glycosylated proteins undergo chaperone-mediated folding. Furthermore, the co-expression of cytosolic chaperones may promote the assembly of virus-like particles.

REFERENCES

Burgers W A, van Harmelen J H, Shephard E, Adams C, Mgwebi T, Bourn W, Hanke T, Williamson A L, Williamson C. 2006. Design and preclinical evaluation of a multigene human immunodeficiency virus type 1 subtype C DNA vaccine for clinical trial. J Gen Virol 87:399-410.

D'Aoust, M. A., Lavoie, P. O., Couture, M. M., Trepanier, S., Guay, J. M., Dargis, M., Mongrand, S., Landry, N., Ward, B. J., Vezina, L. P., 2008. Influenza virus-like particles produced by transient expression in *Nicotiana benthamiana* induce a protective immune response against a lethal viral challenge in mice. Plant Biotechnol J 6, 930-940.

Jutras, P. V., D'Aoust, M. A., Couture, M. M., Vezina, L. P., Goulet, M. C., Michaud, D., Sainsbury, F., 2015. Modulating secretory pathway pH by proton channel co-expression can increase recombinant protein stability in plants. Biotechnol J 10, 1478-1486.

Landry, N., Ward, B. J., Trepanier, S., Montomoli, E., Dargis, M., Lapini, G., Vezina, L. P., 2010. Preclinical and clinical development of plant-made virus-like particle vaccine against avian H5N1 influenza. PLoS One 5, e15559.

MacDonald J, Miletic S, Gaildry T, Chin-Fatt A, Menassa R. 2017. Co-expression with the Type 3 Secretion Chaperone CesT from Enterohemorrhagic *E. coli* Increases Accumulation of Recombinant Tir in Plant Chloroplasts. Front Plant Sci 8:283.

Maclean, J., Koekemoer, M., Olivier, A. J., Stewart, D., Hitzeroth, I I, Rademacher, T., Fischer, R., Williamson, A. L., Rybicki, E. P., 2007. Optimization of human papillomavirus type 16 (HPV-16) L1 expression in plants: comparison of the suitability of different HPV-16 L1 gene variants and different cell-compartment localization. J Gen Virol 88, 1460-1469.

Margolin, E., Chapman, R., Williamson, A. L., Rybicki, E. P., Meyers, A., (submitted for publication to Plant Biotechnology Journal). Production of complex viral glycoproteins in plants as vaccine immunogens.

Sharma, S. K., de Val, N., Bale, S., Guenaga, J., Tran, K., Feng, Y., Dubrovskaya, V., Ward, A. B., Wyatt, R. T., 2015. Cleavage-independent HIV-1 Env trimers engineered as soluble native spike mimetics for vaccine design. Cell Rep 11, 539-550.

Wilbers, R. H., Westerhof, L. B., van Raaij, D. R., van Adrichem, M., Prakasa, A. D., Lozano-Torres, J. L., Bakker, J., Smant, G., Schots, A., 2016. Co-expression of the protease furin in Nicotiana benthamiana leads to efficient processing of latent transforming growth factor-beta1 into a biologically active protein. Plant Biotechnol J 14, 1695-1704.

The invention claimed is:

1. A method of increasing the expression and/or promoting the correct folding of a heterologous polypeptide of interest in a plant cell, the method comprising:
   providing a first nucleic acid encoding a mammalian chaperone protein;
   (ii) providing a second nucleic acid encoding a heterologous polypeptide of interest;
   (iii) cloning the first and second nucleic acids into at least one expression vector adapted to express a polypeptide in a plant cell;
   (iv) transforming or infiltrating a plant cell with the at least one expression vector of step (iii);
   (v) co-expressing the heterologous polypeptide of interest and the polypeptide encoding the mammalian chaperone protein in the plant cell; and
   (vi) recovering the polypeptide of interest from the plant cell,
   wherein the mammalian chaperone protein is selected from calnexin and/or calreticulin.

2. The method of claim 1, wherein the heterologous polypeptide of interest is a glycoprotein.

3. The method of claim 1, wherein the expression of the heterologous polypeptide of interest in the plant cell is increased relative to a control plant cell which has only been transformed with the heterologous polypeptide of interest.

4. The method of claim 1, wherein the co-expression of the heterologous polypeptide of interest and the chaperone protein in the plant cell leads to an at least 1.17-fold increase in the expression of the heterologous polypeptide of interest.

5. The method of claim 1, wherein the at least one expression vector includes promoters and/or other regulators, operably linked to the first nucleic acid and to the second nucleic acid.

6. A plant cell which is transformed with at least one expression vector, comprising:
   a first nucleic acid encoding a mammalian chaperone protein; and
   a second nucleic acid encoding a heterologous polypeptide of interest,
   wherein the mammalian chaperone protein is selected from calnexin and/or calreticulin.

7. The plant cell of claim 6, wherein the heterologous polypeptide of interest is a glycoprotein.

8. The plant cell of claim 6, wherein the expression of the heterologous polypeptide of interest in the plant cell is increased relative to a control plant cell which has only been transformed with the heterologous polypeptide of interest.

9. The plant cell of claim 6, wherein the co-expression of the heterologous polypeptide of interest and the chaperone protein in the plant cell leads to an at least 1.17-fold increase in the expression of the heterologous polypeptide of interest.

10. The plant cell of claim 6, wherein the at least one expression vector includes promoters and/or other regulators, operably linked to the first nucleic acid and to the second nucleic acid.

11. The plant cell of claim 6, wherein the plant cell is from a monocotyledonous or dicotyledonous plant.

12. The plant cell of claim 11, wherein the plant cell is from a plant selected from the group consisting of maize, rice, sorghum, wheat, cassava, barley, oats, rye, sweet potato, soybean, alfalfa, tobacco, sunflower, cotton, and canola.

13. The plant cell of claim 12, wherein the plant cell is from a tobacco plant.

14. A plant comprising the plant cell of claim 6.

* * * * *

SEQUENCE LISTING

<160> NUMBER OF SEQ ID NOS: 22

<210> SEQ ID NO 1
<211> LENGTH: 1266
<212> TYPE: DNA
<213> ORGANISM: Artificial sequence
<220> FEATURE:
<223> OTHER INFORMATION: Nucleotide sequence of humanised calreticulin

<400> SEQUENCE: 1

```
accggtatgc tgctgagcgt gcctctgctg ctggggctgc tggggctggc cgtcgccgaa      60
cctgctgtct acttcaagga acagtttctg gatggcgacg gatggaccag ccggtggatc     120
gagagcaagc acaagtccga tttcggcaag tttgtgctga gctccggcaa gttctatggc     180
gatgaggaga aggacaaggg cctgcagaca agccaggacg cccggttcta cgccctgtct     240
gccagcttcg agccattttc caacaagggc cagaccctgt ggtgcagtt cacagtgaag      300 cacgagcaga acatcgattg cggcggcggc tatgtgaagc tgtttcccaa ttccctggat     360
cagaccgaca tgcacggcga ctctgagtac aacatcatgt tcggcccaga tatctgcggc     420
cccggcacaa agaaggtgca cgtgatcttt aattataagg gcaagaacgt gctgatcaat     480
aaggacatca ggtgtaagga cgatgagttc acccacctgt acacactgat cgtgcgccct     540
gacaacacct atgaggtgaa gatcgataat tcccaggtgg agtccggctc tctggaggac     600
gattgggatt ttctgccccc taagaagatc aaggaccctg atgcctctaa gccagaggac     660
tgggatgaga gggccaagat cgacgatccc acagacagca agcctgagga ctgggataag     720
cccgagcaca tccctgaccc agatgccaag aagcccgaag actgggatga ggagatggat     780
ggcgagtggg agccacccgt gatccagaac cccgagtaca agggcgagtg gaagcctaga     840
cagatcgata tccagacta agggcacc tggatccacc cagagatcga taaccccgag       900
tactctcccg accctagcat ctacgcctat gataattcg gcgtgctggg cctggacctg     960
tggcaggtga agtctggcac catcttcgac aactttctga tcacaaatga tgaggcctac    1020
gccgaggagt ttggcaatga gacatgggc gtgacaaagg ccgccgagaa gcagatgaag    1080
gataagcagg acgaggagca gcggctgaag gaagaggagg aggacaagaa gagaaaggag    1140
gaggaggagg ccgaggataa ggaggacgat gaggacaagg atgaggacga ggaggacgag    1200
gaggataagg aggaagatga agaggaggat gtcccagggc aggcaaaaga tgaactgtga    1260
ctcgag                                                                1266
```

<210> SEQ ID NO 2
<211> LENGTH: 1791
<212> TYPE: DNA
<213> ORGANISM: Artificial sequence
<220> FEATURE:
<223> OTHER INFORMATION: Nucleotide sequence of humanised calnexin

<400> SEQUENCE: 2

```
accggtatgg aggggaaatg gctgctgtgc atgctgctgg tgctgggaac tgctattgtg       60
```
gaggctcacg acggacacga tgacgatgtg attgacatcg aggacgatct ggacgatgtg    120
atcgaggagt tggaggacag caagcctgat accacagccc ccctagctc cccaaaggtg    180 acctacaagg cccccgtgcc tacaggcgag gtgtatttcg ccgactcctt tgatagggc    240 accctgagcg gatggatcct gtccaaggcc aagaaggacg atacagacga tgagatcgcc    300
aagtacgacg gcaagtggga agtggaggag atgaaggagt ctaagctgcc tggcgataag    360
ggcctggtgc tgatgtcccg ggccaagcac acgccatct ctgccaagct gaataagcca    420
ttcctgtttg acaccaagcc cctgatcgtg cagtacgagg tgaacttcca gaatggcatc    480
gagtgcggcg cgcctatgt gaagctgctg tccaagacac agagctgaa tctggaccag    540 ttccacgata agacccctta cacaatcatg tttggcccag acaagtgtgg cgaggattat    600
aagctgcact tcatctttag acacaagaac ccaaagaccg gcatctatga ggagaagcac    660
gccaagaggc ccgacgccga tctgaagacc tacttcacag acaagaagac ccacctgtat    720
acactgatcc tgaacccaga caattctttt gagatcctgg tggatcagtc cgtggtgaac    780
tctggcaatc tgctgaacga tatgacccca cccgtgaatc ccagcaggga gatcgaggac    840
cccgaggatc gcaagcctga ggactgggat gagcggccca gatcccaga cccagaggca    900 gtgaagcctg acgattggga cgaggatgcc cctgccaaga tcccagatga ggaggccaca    960
aagcccgagg gctggctgga cgatgagcct gagtacgtgc ctgacccaga tgccgagaag   1020
cccgaggact gggatgagga catggatggc gagtgggagg ccccacagat cgcaaaccca   1080
agatgcgaga gcgcccctgg atgtggcgtg tggcagaggc ctgtgatcga caacccaaat   1140
tacaagggca gtggaagcc tccaatgatc gataatccat cctatcaggg catctggaag   1200
ccccgcaaga tccccaaccc tgacttcttt gaggatctgg agcccttccg gatgaccct   1260 ttttctgcca tcggcctgga gctgtggtct atgacaagcg acatcttctt tgataacttc   1320
atcatctgcg ccgaccggag aatcgtggac gattgggcca acgacggatg gggcctgaag   1380
aaggcagcag atggagcagc agagccagga gtggtgggac agatgatcga ggcagcagag   1440
gagcggccct ggctgtgggt ggtgtacatc ctgaccgtgg ccctgcccgt gttcctggtc   1500
atcctgttct gctgttctgg caagaagcag accagcggca tggagtataa gagacagac    1560 gcccccacagc ccgatgtgaa gaggaggag gaggagaagg aggaggagaa ggacaaggc    1620 gatgaggagg aggagggcga ggagaagctg gaggagaagc agaagagcga cgccgaggag    1680
gatggcggca gtgtcccca ggaggaggag gaccggaagc ctaaggcaga agaagacgaa    1740
atcctgaatc ggtcaccaag aaatagaaaa ccacggaggg aatgactcga g             1791

<210> SEQ ID NO 3
<211> LENGTH: 417
<212> TYPE: PRT
<213> ORGANISM: Homo sapiens

<400> SEQUENCE: 3

Met Leu Leu Ser Val Pro Leu Leu Gly Leu Gly Leu Ala Val
1               5                   10                  15

Ala Glu Pro Ala Val Tyr Phe Lys Glu Gln Phe Leu Asp Gly Asp Gly
            20                  25                  30

Trp Thr Ser Arg Trp Ile Glu Ser Lys His Lys Ser Asp Phe Gly Lys
        35                  40                  45

Phe Val Leu Ser Ser Gly Lys Phe Tyr Gly Asp Glu Glu Lys Asp Lys
    50                  55                  60

-continued

```
Gly Leu Gln Thr Ser Gln Asp Ala Arg Phe Tyr Ala Leu Ser Ala Ser
 65                  70                  75                  80

Phe Glu Pro Phe Ser Asn Lys Gly Gln Thr Leu Val Val Gln Phe Thr
                 85                  90                  95

Val Lys His Glu Gln Asn Ile Asp Cys Gly Gly Gly Tyr Val Lys Leu
            100                 105                 110

Phe Pro Asn Ser Leu Asp Gln Thr Asp Met His Gly Asp Ser Glu Tyr
        115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
    210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
    290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Glu Ala Glu Asp
    370                 375                 380

Lys Glu Asp Asp Glu Asp Lys Asp Glu Asp Glu Glu Asp Glu Glu Asp
385                 390                 395                 400

Lys Glu Glu Asp Glu Glu Glu Asp Val Pro Gly Gln Ala Lys Asp Glu
                405                 410                 415

Leu
```

<210> SEQ ID NO 4
<211> LENGTH: 592
<212> TYPE: PRT
<213> ORGANISM: Homo sapiens

<400> SEQUENCE: 4

```
Met Glu Gly Lys Trp Leu Leu Cys Met Leu Leu Val Leu Gly Thr Ala
 1               5                  10                  15
```

```
Ile Val Glu Ala His Asp Gly His Asp Asp Val Ile Asp Ile Glu
             20                  25                  30
Asp Asp Leu Asp Asp Val Ile Glu Glu Val Glu Asp Ser Lys Pro Asp
         35                  40                  45
Thr Thr Ala Pro Pro Ser Ser Pro Lys Val Thr Tyr Lys Ala Pro Val
     50                  55                  60
Pro Thr Gly Glu Val Tyr Phe Ala Asp Ser Phe Asp Arg Gly Thr Leu
 65                  70                  75                  80
Ser Gly Trp Ile Leu Ser Lys Ala Lys Lys Asp Asp Thr Asp Asp Glu
                 85                  90                  95
Ile Ala Lys Tyr Asp Gly Lys Trp Glu Val Glu Glu Met Lys Glu Ser
             100                 105                 110
Lys Leu Pro Gly Asp Lys Gly Leu Val Leu Met Ser Arg Ala Lys His
         115                 120                 125
His Ala Ile Ser Ala Lys Leu Asn Lys Pro Phe Leu Phe Asp Thr Lys
     130                 135                 140
Pro Leu Ile Val Gln Tyr Glu Val Asn Phe Gln Asn Gly Ile Glu Cys
145                 150                 155                 160
Gly Gly Ala Tyr Val Lys Leu Leu Ser Lys Thr Pro Glu Leu Asn Leu
                 165                 170                 175
Asp Gln Phe His Asp Lys Thr Pro Tyr Thr Ile Met Phe Gly Pro Asp
             180                 185                 190
Lys Cys Gly Glu Asp Tyr Lys Leu His Phe Ile Phe Arg His Lys Asn
         195                 200                 205
Pro Lys Thr Gly Ile Tyr Glu Glu Lys His Ala Lys Arg Pro Asp Ala
     210                 215                 220
Asp Leu Lys Thr Tyr Phe Thr Asp Lys Lys Thr His Leu Tyr Thr Leu
225                 230                 235                 240
Ile Leu Asn Pro Asp Asn Ser Phe Glu Ile Leu Val Asp Gln Ser Val
                245                 250                 255
Val Asn Ser Gly Asn Leu Leu Asn Asp Met Thr Pro Pro Val Asn Pro
             260                 265                 270
Ser Arg Glu Ile Glu Asp Pro Glu Asp Arg Lys Pro Glu Asp Trp Asp
         275                 280                 285
Glu Arg Pro Lys Ile Pro Asp Pro Glu Ala Val Lys Pro Asp Asp Trp
     290                 295                 300
Asp Glu Asp Ala Pro Ala Lys Ile Pro Asp Glu Ala Thr Lys Pro
305                 310                 315                 320
Glu Gly Trp Leu Asp Asp Glu Pro Glu Tyr Val Pro Asp Pro Asp Ala
                325                 330                 335
Glu Lys Pro Glu Asp Trp Asp Glu Asp Met Asp Gly Glu Trp Glu Ala
             340                 345                 350
Pro Gln Ile Ala Asn Pro Arg Cys Glu Ser Ala Pro Gly Cys Gly Val
         355                 360                 365
Trp Gln Arg Pro Val Ile Asp Asn Pro Asn Tyr Lys Gly Lys Trp Lys
     370                 375                 380
Pro Pro Met Ile Asp Asn Pro Ser Tyr Gln Gly Ile Trp Lys Pro Arg
385                 390                 395                 400
Lys Ile Pro Asn Pro Asp Phe Phe Glu Asp Leu Glu Pro Phe Arg Met
                405                 410                 415
Thr Pro Phe Ser Ala Ile Gly Leu Glu Leu Trp Ser Met Thr Ser Asp
             420                 425                 430
Ile Phe Phe Asp Asn Phe Ile Ile Cys Ala Asp Arg Arg Ile Val Asp
```

```
                   435                 440                 445
Asp Trp Ala Asn Asp Gly Trp Gly Leu Lys Lys Ala Ala Asp Gly Ala
        450                 455                 460
Ala Glu Pro Gly Val Val Gly Gln Met Ile Glu Ala Ala Glu Glu Arg
465                 470                 475                 480
Pro Trp Leu Trp Val Val Tyr Ile Leu Thr Val Ala Leu Pro Val Phe
                485                 490                 495
Leu Val Ile Leu Phe Cys Cys Ser Gly Lys Lys Gln Thr Ser Gly Met
            500                 505                 510
Glu Tyr Lys Lys Thr Asp Ala Pro Gln Pro Asp Val Lys Glu Glu Glu
        515                 520                 525
Glu Glu Lys Glu Glu Lys Asp Lys Gly Asp Glu Glu Glu Glu Glu Gly
    530                 535                 540
Glu Glu Lys Leu Glu Glu Lys Gln Lys Ser Asp Ala Glu Glu Asp Gly
545                 550                 555                 560
Gly Thr Val Ser Gln Glu Glu Asp Arg Lys Pro Lys Ala Glu Glu
                565                 570                 575
Asp Glu Ile Leu Asn Arg Ser Pro Arg Asn Arg Lys Pro Arg Arg Glu
            580                 585                 590

<210> SEQ ID NO 5
<211> LENGTH: 2183
<212> TYPE: DNA
<213> ORGANISM: Artificial sequence
<220> FEATURE:
<223> OTHER INFORMATION: Nucleotide sequence of CAP256 SU gp120-HA2
      including terminal restriction sites

<400> SEQUENCE: 5
tcatgaaagc ttaccggtgc caccatggag tggtcttgga tcttcctgtt tctgctgagc        60
gggactgctg agtgcattc ttccggaggg ctgtgggtca ctgtctacta ggcgtgcct        120 gtctggagag aggccaagac cacactgttc tgcgcttccg atgcaaagtc ttacgaaaaa        180
gaggtgcaca acgtctgggc cacacatgct tgcgtgccaa ctgaccccaa ccctcaggaa        240
ctggtgctga gaatgtcac cgagaacttt aatatgtgga aaaatgacat ggtggatcag        300
atgcacgagg atatcattag tctgtgggac cagtcactga gccctgcgt gaaactgaca        360 cctctgtgcg tcactctgaa ctgtagcgat gcaaaggtga acattaatgc acatacaat        420 ggcactcgcg aggaaatcaa aaactgttcc ttcaatgcaa ctaccgaact gagggacaag        480
aagaagaagg agtacgccct gttttatcgc ctggacatcg tgccctgaa caaggaaggg        540 aacaataaca gtgagtatcg gctgattaac tgcaatacca gcgtgattac ccaggcctgt        600
cctaaagtca ccttcgatcc aattcccatc cactactgcg caccagccgg atatgctatt        660
ctgaagtgta acaacaaaac ttttaacggg accggaccct gcaataacgt gtctacagtc        720
cagtgtactc atggcatcaa gcctgtggtc tcaacccagc tgctgctgaa tgggagcctg        780
gccgaggaag agatcattat cagaagcgag aacctgaccg acaatgtgaa gacaattatc        840
gtccacctga cgaatccgt ggagattaat tgcaccaggc aaacaacaa cacacgaaaa        900 tctattcgga tcggaccagg acagaccttc tacgcaacag ggacattat cggagatatc        960 aggcaggctc attgtaacat tctgaaatc aagtgggaga aaccctgca gcgcgtgagt       1020 gaaaagctgc gagagcactt caacaaaaca atcatcttta tcagagctc cggcggggac       1080 ctggaaatca aactcatcc attcaactgc ggaggcgagt tctttactg taacactagc       1140 gatctgttct taataagac ctttgacgag acctattcca caggctcaaa cagcactaat       1200
```

```
tctaccatta cactgccatg ccgaatcaaa cagattatca acatgtggca ggaagtgggc    1260
cgggcaatgt atgccagccc cattgccgga gagatcacct gtaagtccaa tatcactgga    1320
ctgctgctga ccagagatgg gggaggcaac aattctactg aagagaccct taggcccggg    1380
ggaggcaaca tgagagacaa ttggaggagc gaactgtaca agtataaagt ggtcgaggtg    1440
aagcctctgg gaatcgcacc aaccgaggcc cggagaaggg tggtccagca gggcggtgga    1500
ggctcaggtg gaggcggatc cgaggggggga tggcagggaa tggtggacgg gtggtacgga    1560
```

```
Asn Lys Glu Gly Asn Asn Asn Ser Glu Tyr Arg Leu Ile Asn Cys Asn
            180                 185                 190

Thr Ser Val Ile Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
        210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
            245                 250                 255

Asn Gly Ser Leu Ala Glu Glu Ile Ile Arg Ser Glu Asn Leu
            260                 265                 270

Thr Asp Asn Val Lys Thr Ile Ile Val His Leu Asn Glu Ser Val Glu
        275                 280                 285

Ile Asn Cys Thr Arg Pro Asn Asn Asn Thr Arg Lys Ser Ile Arg Ile
        290                 295                 300

Gly Pro Gly Gln Thr Phe Tyr Ala Thr Gly Asp Ile Ile Gly Asp Ile
305                 310                 315                 320

Arg Gln Ala His Cys Asn Ile Ser Glu Ile Lys Trp Glu Lys Thr Leu
            325                 330                 335

Gln Arg Val Ser Glu Lys Leu Arg Glu His Phe Asn Lys Thr Ile Ile
            340                 345                 350

Phe Asn Gln Ser Ser Gly Gly Asp Leu Glu Ile Thr Thr His Ser Phe
        355                 360                 365

Asn Cys Gly Gly Glu Phe Phe Tyr Cys Asn Thr Ser Asp Leu Phe Phe
370                 375                 380

Asn Lys Thr Phe Asp Glu Thr Tyr Ser Thr Gly Ser Asn Ser Thr Asn
385                 390                 395                 400

Ser Thr Ile Thr Leu Pro Cys Arg Ile Lys Gln Ile Ile Asn Met Glu
            405                 410                 415

Thr Trp Gln Glu Val Gly Arg Ala Met Glu Thr Tyr Ala Ser Pro Ile
            420                 425                 430

Ala Gly Glu Ile Thr Cys Lys Ser Asn Ile Thr Gly Leu Leu Leu Thr
            435                 440                 445

Arg Asp Gly Gly Gly Asn Asn Ser Thr Glu Glu Thr Phe Arg Pro Gly
            450                 455                 460

Gly Gly Asn Met Glu Thr Arg Asp Asn Trp Arg Ser Glu Leu Tyr Lys
465                 470                 475                 480

Tyr Lys Val Val Glu Val Lys Pro Leu Gly Ile Ala Pro Thr Glu Ala
            485                 490                 495

Arg Arg Arg Val Val Gln Gln Gly Gly Gly Ser Gly Gly Gly Gly
            500                 505                 510

Ser Glu Gly Gly Trp Gln Gly Met Glu Thr Val Asp Gly Trp Tyr Gly
            515                 520                 525

Tyr His His Ser Asn Glu Gln Gly Ser Gly Tyr Ala Ala Asp Lys Glu
            530                 535                 540

Ser Thr Gln Lys Ala Ile Asp Gly Val Thr Asn Lys Val Asn Ser Ile
545                 550                 555                 560

Ile Asp Lys Met Glu Thr Asn Thr Gln Phe Glu Ala Val Gly Arg Glu
            565                 570                 575

Phe Asn Asn Leu Glu Arg Arg Ile Glu Asn Leu Asn Lys Lys Met Glu
            580                 585                 590

Thr Glu Asp Gly Phe Leu Asp Val Trp Thr Tyr Asn Ala Glu Leu Leu
```

```
                  595                 600                 605
Val Leu Met Glu Thr Glu Asn Glu Arg Thr Leu Asp Phe His Asp Ser
    610                 615                 620

Asn Val Lys Asn Leu Tyr Asp Lys Val Arg Leu Gln Leu Arg Asp Asn
625                 630                 635                 640

Ala Lys Glu Leu Gly Asn Gly Cys Phe Glu Phe Tyr His Lys Cys Asp
                645                 650                 655

Asn Glu Cys Met Glu Thr Glu Ser Val Arg Asn Gly Thr Tyr Asp Tyr
                660                 665                 670

Pro Gln Tyr Ser Glu Glu Ala Arg Leu Lys Arg Glu Glu Ile Ser Gly
                675                 680                 685

Val Lys Leu Glu Ser Ile Gly Ile Tyr Gln Ile Leu Ser Ile Tyr Ser
    690                 695                 700

Thr Val Ala Ser Ser Leu Ala Leu Ala Ile Met Glu Thr Val Ala Gly
705                 710                 715                 720

Leu Ser Leu Trp Met Glu Thr Cys Ser Asn Gly Ser Leu Gln Cys Arg
                725                 730                 735

Ala Ala Ala

<210> SEQ ID NO 7
<211> LENGTH: 512
<212> TYPE: DNA
<213> ORGANISM: Artificial sequence
<220> FEATURE:
<223> OTHER INFORMATION: Nucleotide sequence for gp41tr fragment

<400> SEQUENCE: 7
tccggagtcg gatccgctgt ggtcggactg ggagcagtgt tcctggggtt tctgggaact    60
gctggcagca ccatgggagc cgcttccatt actctgaccg tgcaggcacg ccagctgctg   120
tctggcatcg tccagcagca gagtaacctg ctgcgggctc ctgaagcaca gcagcatatg   180
ctgcagctga ccgtgtgggg gattaagcag ctgcaggccc gggtcctggc tatcgagaga   240
tacctgaagg atcagcagct gctggggatg tggggatgca gtggcaaact gatttgcacc   300
acaaacgtgt actggaacag cagctggtcc aacaagacat ataatgaaat ctgggacaac   360
atgacttgga tgcagtggga ccgcgagatc gataactaca cagacactat ctataaactg   420
ctggaagtct cacagaaaca gcaggagtca atgaaaagg acctgctggc actggatgcg   480
gccgcatgat ttttctgaat tctagactcg ag                                 512

<210> SEQ ID NO 8
<211> LENGTH: 167
<212> TYPE: PRT
<213> ORGANISM: Artificial sequence
<220> FEATURE:
<223> OTHER INFORMATION: Amino acid sequence of gp41tr fragment

<400> SEQUENCE: 8

Ala Val Val Gly Leu Gly Ala Val Phe Leu Gly Phe Leu Gly Thr Ala
1               5                   10                  15

Gly Ser Thr Met Glu Thr Gly Ala Ala Ser Ile Thr Leu Thr Val Gln
            20                  25                  30

Ala Arg Gln Leu Leu Ser Gly Ile Val Gln Gln Gln Ser Asn Leu Leu
        35                  40                  45

Arg Ala Pro Glu Ala Gln Gln His Met Glu Thr Leu Gln Leu Thr Val
    50                  55                  60

Trp Gly Ile Lys Gln Leu Gln Ala Arg Val Leu Ala Ile Glu Arg Tyr
```

```
                65                  70                  75                  80
Leu Lys Asp Gln Gln Leu Leu Gly Met Glu Thr Trp Gly Cys Ser Gly
                    85                  90                  95

Lys Leu Ile Cys Thr Thr Asn Val Tyr Trp Asn Ser Ser Trp Ser Asn
                100                 105                 110

Lys Thr Tyr Asn Glu Ile Trp Asp Asn Met Glu Thr Thr Trp Met Glu
                115                 120                 125

Thr Gln Trp Asp Arg Glu Ile Asp Asn Tyr Thr Asp Thr Ile Tyr Lys
            130                 135                 140

Leu Leu Glu Val Ser Gln Lys Gln Glu Ser Asn Glu Lys Asp Leu
145                 150                 155                 160

Leu Ala Leu Asp Ala Ala Ala
                165
```

<210> SEQ ID NO 9
<211> LENGTH: 852
<212> TYPE: DNA
<213> ORGANISM: Artificial sequence
<220> FEATURE:
<223> OTHER INFORMATION: Nucleotide sequence for gp120 backbone
      including restriction sites

<400> SEQUENCE: 9

```
tcatgaaagc ttaccggtgc caccatggag tggtcttgga tcttcctgtt tctgctgagc     60
gggactgctg gagtgcattc ttccggaggg ctgtgggtca ctgtctacta tggcgtgcct    120
gtctggagag aggccaagac cacactgttc tgcgcttccg atgcaaagtc ttacgaaaaa    180
gaggtgcaca acgtctgggc cacacatgct tgcgtgccaa ctgaccccaa ccctcaggaa    240
ctggtgctga gaatgtcac cgagaacttt aatatgtgga aaatgacat ggtggatcag     300
atgcacgagg atatcattag tctgtgggac cagtcactga gccctgcgt gaaactgaca    360
cctctgtgcg tcactctgaa ctgtagcgat gcaaaggtga acattaatgc cacatacaat    420
ggcactcgcg aggaaatcaa aaactgttcc ttcaatgcaa ctaccgaact gagggacaag    480
aagaagaagg agtacgccct gttttatcgc ctggacatcg tgccctgaa caaggaaggg    540
aacaataaca gtgagtatcg gctgattaac tgcaatacca gcgtgattac ccaggcctgt    600
cctaaagtca ccttcgatcc aattcccatc cactactgcg caccagccgg atatgctatt    660
ctgaagtgta caacaaaac tttaacggg accggacct gcaataacgt gtctacagtc      720
cagtgtactc atggcatcaa gcctgtggtc tcaacccagc tgctgctgaa tgggagcctg    780
gccgaggaag agatcattat cagaagcgag aacctgaccg acaatgtgaa gacaattatc    840
gtccacctga ac                                                         852
```

<210> SEQ ID NO 10
<211> LENGTH: 513
<212> TYPE: PRT
<213> ORGANISM: Artificial sequence
<220> FEATURE:
<223> OTHER INFORMATION: Amino acid sequence for gp120 backbone
      including restriction sites

<400> SEQUENCE: 10

```
Met Glu Thr Glu Trp Ser Trp Ile Phe Leu Phe Leu Leu Ser Gly Thr
1               5                   10                  15

Ala Gly Val His Ser Ser Gly Gly Leu Trp Val Thr Val Tyr Tyr Gly
            20                  25                  30

Val Pro Val Trp Arg Glu Ala Lys Thr Thr Leu Phe Cys Ala Ser Asp
```

```
              35                  40                  45
Ala Lys Ser Tyr Glu Lys Glu Val His Asn Val Trp Ala Thr His Ala
 50                  55                  60

Cys Val Pro Thr Asp Pro Asn Pro Gln Glu Leu Val Leu Lys Asn Val
 65                  70                  75                  80

Thr Glu Asn Phe Asn Met Glu Thr Trp Lys Asn Asp Met Glu Thr Val
                     85                  90                  95

Asp Gln Met Glu Thr His Glu Asp Ile Ile Ser Leu Trp Asp Gln Ser
                100                 105                 110

Leu Lys Pro Cys Val Lys Leu Thr Pro Leu Cys Val Thr Leu Asn Cys
                115                 120                 125

Ser Asp Ala Lys Val Asn Ile Asn Ala Thr Tyr Asn Gly Thr Arg Glu
130                 135                 140

Glu Ile Lys Asn Cys Ser Phe Asn Ala Thr Thr Glu Leu Arg Asp Lys
145                 150                 155                 160

Lys Lys Lys Glu Tyr Ala Leu Phe Tyr Arg Leu Asp Ile Val Pro Leu
                165                 170                 175

Asn Lys Glu Gly Asn Asn Asn Ser Glu Tyr Arg Leu Ile Asn Cys Asn
                180                 185                 190

Thr Ser Val Ile Thr Gln Ala Cys Pro Lys Val Thr Phe Asp Pro Ile
                195                 200                 205

Pro Ile His Tyr Cys Ala Pro Ala Gly Tyr Ala Ile Leu Lys Cys Asn
210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Glu Ile Ile Ile Arg Ser Glu Asn Leu
                260                 265                 270

Thr Asp Asn Val Lys Thr Ile Ile Val His Leu Asn Glu Ser Val Glu
                275                 280                 285

Ile Asn Cys Thr Arg Pro Asn Asn Asn Thr Arg Lys Ser Ile Arg Ile
290                 295                 300

Gly Pro Gly Gln Thr Phe Tyr Ala Thr Gly Asp Ile Ile Gly Asp Ile
305                 310                 315                 320

Arg Gln Ala His Cys Asn Ile Ser Glu Ile Lys Trp Glu Lys Thr Leu
                325                 330                 335

Gln Arg Val Ser Glu Lys Leu Arg Glu His Phe Asn Lys Thr Ile Ile
                340                 345                 350

Phe Asn Gln Ser Ser Gly Gly Asp Leu Glu Ile Thr Thr His Ser Phe
                355                 360                 365

Asn Cys Gly Gly Glu Phe Phe Tyr Cys Asn Thr Ser Asp Leu Phe Phe
                370                 375                 380

Asn Lys Thr Phe Asp Glu Thr Tyr Ser Thr Gly Ser Asn Ser Thr Asn
385                 390                 395                 400

Ser Thr Ile Thr Leu Pro Cys Arg Ile Lys Gln Ile Ile Asn Met Glu
                405                 410                 415

Thr Trp Gln Glu Val Gly Arg Ala Met Glu Thr Tyr Ala Ser Pro Ile
                420                 425                 430

Ala Gly Glu Ile Thr Cys Lys Ser Asn Ile Thr Gly Leu Leu Leu Thr
                435                 440                 445

Arg Asp Gly Gly Gly Asn Asn Ser Thr Glu Glu Thr Phe Arg Pro Gly
450                 455                 460
```

Gly Gly Asn Met Glu Thr Arg Asp Asn Trp Arg Ser Glu Leu Tyr Lys
465                 470                 475                 480

Tyr Lys Val Val Glu Val Lys Pro Leu Gly Ile Ala Pro Thr Glu Ala
            485                 490                 495

Arg Arg Arg Val Val Gln Gln Gly Gly Gly Ser Gly Gly Gly Gly
            500                 505                 510

Ser

<210> SEQ ID NO 11
<211> LENGTH: 2018
<212> TYPE: DNA
<213> ORGANISM: Artificial sequence
<220> FEATURE:
<223> OTHER INFORMATION: Nucleotide sequence of CAP 256 SU gp140NFL

<400> SEQUENCE: 11

| | | |
|---|---|---|
| tcatgaaagc ttaccggtgc caccatggag tggtcttgga tcttcctgtt tctgctgagc | 60 |
| gggactgctg gagtgcattc ttccggaggg ctgtgggtca ctgtctacta tggcgtgcct | 120 |
| gtctggagag aggccaagac cacactgttc tgcgcttccg atgcaaagtc ttacgaaaaa | 180 |
| gaggtgcaca acgtctgggc cacacatgct tgcgtgccaa ctgaccccaa ccctcaggaa | 240 |
| ctggtgctga gaatgtcac cgagaacttt aatatgtgga aaatgacat ggtggatcag | 300 |
| atgcacgagg atatccattag tctgtgggac cagtcactga gccctgcgt gaaactgaca | 360 |
| cctctgtgcg tcactctgaa ctgtagcgat gcaaaggtga acattaatgc cacatacaat | 420 |
| ggcactcgcg aggaaatcaa aaactgttcc ttcaatgcaa ctaccgaact gagggacaag | 480 |
| aagaagaagg agtacgccct gttttatcgc ctggacatcg tgccctgaa caaggaaggg | 540 |
| aacaataaca gtgagtatcg gctgattaac tgcaatacca gcgtgattac ccaggcctgt | 600 |
| cctaaagtca ccttcgatcc aattcccatc cactactgcg caccagccgg atatgctatt | 660 |
| ctgaagtgta caacaaaaac ttttaacggg accggaccct gcaataacgt gtctacagtc | 720 |
| cagtgtactc atggcatcaa gcctgtggtc tcaacccagc tgctgctgaa tgggagcctg | 780 |
| gccgaggaag agatcattat cagaagcgag aacctgaccg acaatgtgaa gacaattatc | 840 |
| gtccacctga cgaatccgt ggagattaat tgcaccaggc aaacaacaa cacacgaaaa | 900 |
| tctattcgga tcggaccagg acagaccttc tacgcaacag gggacattat cggagatatc | 960 |
| aggcaggctc attgtaacat ttctgaaatc aagtgggaga aaccctgca gcgcgtgagt | 1020 |
| gaaaagctgc gagagcactt caacaaaaca atcatcttta atcagagctc cggcggggac | 1080 |
| ctggaaatca caactcattc attcaactgc ggaggcgagt tcttttactg taacactagc | 1140 |
| gatctgttct ttaataagac ctttgacgag acctattcca caggctcaaa cagcactaat | 1200 |
| tctaccatta cactgccatg ccgaatcaaa cagattatca acatgtggca ggaagtgggc | 1260 |
| cgggcaatgt atgccagccc cattgccgga gagatcacct gtaagtccaa tatcactgga | 1320 |
| ctgctgctga ccagagatgg gggaggcaac aattctactg aagagacctt taggcccggg | 1380 |
| ggaggcaaca tgagagacaa ttggaggagc gaactgtaca gtataaagt ggtcgaggtg | 1440 |
| aagcctctgg gaatcgcacc aaccgaggcc cggagaaggg tggtccagca gggcggtgga | 1500 |
| ggctcaggtg gaggcggatc cgctgtggtc ggactgggag cagtgttcct ggggtttctg | 1560 |
| ggaactgctg gcagcaccat gggagccgct tccattactc tgaccgtgca ggcacgccag | 1620 |
| ctgctgtctg gcatcgtcca gcagcagagt aacctgctgc gggctcctga agcacagcag | 1680 |
| catatgctgc agctgaccgt gtggggggatt aagcagctgc aggcccgggt cctggctatc | 1740 |

```
gagagatacc tgaaggatca gcagctgctg gggatgtggg gatgcagtgg caaactgatt    1800
tgcaccacaa acgtgtactg gaacagcagc tggtccaaca agacatataa tgaaatctgg    1860
gacaacatga cttggatgca gtgggaccgc gagatcgata actacacaga cactatctat    1920
aaactgctgg aagtctcaca gaaacagcag gagtcaaatg aaaaggacct gctggcactg    1980
gatgcggccg catgattttt ctgaattcta gactcgag                            2018
```

<210> SEQ ID NO 12
<211> LENGTH: 656
<212> TYPE: PRT
<213> ORGANISM: Artificial sequence
<220> FEATURE:
<223> OTHER INFORMATION: Amino acid sequence of CAP256 SU gp140NFL

<400> SEQUENCE: 12

```
Met Glu Trp Ser Trp Ile Phe Leu Phe Leu Leu Ser Gly Thr Ala Gly
1               5                   10                  15

Val His Ser Ser Gly Gly Leu Trp Val Thr Val Tyr Tyr Gly Val Pro
            20                  25                  30

Val Trp Arg Glu Ala Lys Thr Thr Leu Phe Cys Ala Ser Asp Ala Lys
        35                  40                  45

Ser Tyr Glu Lys Glu Val His Asn Val Trp Ala Thr His Ala Cys Val
    50                  55                  60

Pro Thr Asp Pro Asn Pro Gln Glu Leu Val Leu Lys Asn Val Thr Glu
65                  70                  75                  80

Asn Phe Asn Met Trp Lys Asn Asp Met Val Asp Gln Met His Glu Asp
                85                  90                  95

Ile Ile Ser Leu Trp Asp Gln Ser Leu Lys Pro Cys Val Lys Leu Thr
            100                 105                 110

Pro Leu Cys Val Thr Leu Asn Cys Ser Asp Ala Lys Val Asn Ile Asn
        115                 120                 125

Ala Thr Tyr Asn Gly Thr Arg Glu Glu Ile Lys Asn Cys Ser Phe Asn
    130                 135                 140

Ala Thr Thr Glu Leu Arg Asp Lys Lys Lys Glu Tyr Ala Leu Phe
145                 150                 155                 160

Tyr Arg Leu Asp Ile Val Pro Leu Asn Lys Glu Gly Asn Asn Ser
                165                 170                 175

Glu Tyr Arg Leu Ile Asn Cys Asn Thr Ser Val Ile Thr Gln Ala Cys
            180                 185                 190

Pro Lys Val Thr Phe Asp Pro Ile Pro Ile His Tyr Cys Ala Pro Ala
        195                 200                 205

Gly Tyr Ala Ile Leu Lys Cys Asn Asn Lys Thr Phe Asn Gly Thr Gly
    210                 215                 220

Pro Cys Asn Asn Val Ser Thr Val Gln Cys Thr His Gly Ile Lys Pro
225                 230                 235                 240

Val Val Ser Thr Gln Leu Leu Leu Asn Gly Ser Leu Ala Glu Glu Glu
                245                 250                 255

Ile Ile Ile Arg Ser Glu Asn Leu Thr Asp Asn Val Lys Thr Ile Ile
            260                 265                 270

Val His Leu Asn Glu Ser Val Glu Ile Asn Cys Thr Arg Pro Asn Asn
        275                 280                 285

Asn Thr Arg Lys Ser Ile Arg Ile Gly Pro Gly Gln Thr Phe Tyr Ala
    290                 295                 300

Thr Gly Asp Ile Ile Gly Asp Ile Arg Gln Ala His Cys Asn Ile Ser
```

Glu Ile Lys Trp Glu Lys Thr Leu Gln Arg Val Ser Glu Lys Leu Arg
305                 310                 315                 320

Glu His Phe Asn Lys Thr Ile Ile Phe Asn Gln Ser Ser Gly Gly Asp
        325                 330                 335

Leu Glu Ile Thr Thr His Ser Phe Asn Cys Gly Gly Glu Phe Phe Tyr
            340                 345                 350

Cys Asn Thr Ser Asp Leu Phe Phe Asn Lys Thr Phe Asp Glu Thr Tyr
355                 360                 365

Ser Thr Gly Ser Asn Ser Thr Asn Ser Thr Ile Thr Leu Pro Cys Arg
    370                 375                 380

Ile Lys Gln Ile Ile Asn Met Trp Gln Glu Val Gly Arg Ala Met Tyr
385                 390                 395                 400

Ala Ser Pro Ile Ala Gly Glu Ile Thr Cys Lys Ser Asn Ile Thr Gly
        405                 410                 415

Leu Leu Leu Thr Arg Asp Gly Gly Asn Asn Ser Thr Glu Glu Thr
            420                 425                 430

Phe Arg Pro Gly Gly Gly Asn Met Arg Asp Asn Trp Arg Ser Glu Leu
435                 440                 445

Tyr Lys Tyr Lys Val Val Glu Val Lys Pro Leu Gly Ile Ala Pro Thr
    450                 455                 460

Glu Ala Arg Arg Val Val Gln Gln Gly Gly Gly Ser Gly Gly
465                 470                 475                 480

Gly Gly Ser Ala Val Val Gly Leu Gly Ala Val Phe Leu Gly Phe Leu
        485                 490                 495

Gly Thr Ala Gly Ser Thr Met Gly Ala Ala Ser Ile Thr Leu Thr Val
            500                 505                 510

Gln Ala Arg Gln Leu Leu Ser Gly Ile Val Gln Gln Ser Asn Leu
515                 520                 525

Leu Arg Ala Pro Glu Ala Gln Gln His Met Leu Gln Leu Thr Val Trp
    530                 535                 540

Gly Ile Lys Gln Leu Gln Ala Arg Val Leu Ala Ile Glu Arg Tyr Leu
545                 550                 555                 560

Lys Asp Gln Gln Leu Leu Gly Met Trp Gly Cys Ser Gly Lys Leu Ile
        565                 570                 575

Cys Thr Thr Asn Val Tyr Trp Asn Ser Ser Trp Ser Asn Lys Thr Tyr
            580                 585                 590

Asn Glu Ile Trp Asp Asn Met Thr Trp Met Gln Trp Asp Arg Glu Ile
595                 600                 605

Asp Asn Tyr Thr Asp Thr Ile Tyr Lys Leu Leu Glu Val Ser Gln Lys
    610                 615                 620

Gln Gln Glu Ser Asn Glu Lys Asp Leu Leu Ala Leu Asp Ala Ala Ala
625                 630                 635                 640
                645                 650                 655

<210> SEQ ID NO 13
<211> LENGTH: 192
<212> TYPE: DNA
<213> ORGANISM: Human Immunodeficiency virus

<400> SEQUENCE: 13
atgacagtga cggggacatg gaggaattat caacaatggt ggatatgggg aatcttaggc    60
ttttggatgc taatgatttg taatggcttg tgggttacag tctactatgg ggtacctgtg   120
tggagagaag caaaaactac tctattttgt gcctcagacg ctaaatcata tgagaaagag   180
gtgcataatg tc                                              192

<210> SEQ ID NO 14
<211> LENGTH: 853
<212> TYPE: PRT
<213> ORGANISM: Human immunodeficiency virus

<400> SEQUENCE: 14

Met Thr Val Thr Gly Thr Trp Arg Asn Tyr Gln Gln Trp Trp Ile Trp
1               5                   10                  15

Gly Ile Leu Gly Phe Trp Met Leu Met Ile Cys Asn Gly Leu Trp Val
            20                  25                  30

Thr Val Tyr Tyr Gly Val Pro Val Trp Arg Glu Ala Lys Thr Thr Leu
        35                  40                  45

Phe Cys Ala Ser Asp Ala Lys Ser Tyr Glu Lys Glu Val His Asn Val
    50                  55                  60

Trp Ala Thr His Ala Cys Val Pro Thr Asp Pro Asn Pro Gln Glu Leu
65                  70                  75                  80

Val Leu Lys Asn Val Thr Glu Asn Phe Asn Met Trp Lys Asn Asp Met
                85                  90                  95

Val Asp Gln Met His Glu Asp Ile Ile Ser Leu Trp Asp Gln Ser Leu
            100                 105                 110

Lys Pro Cys Val Lys Leu Thr Pro Leu Cys Val Thr Leu Asn Cys Ser
        115                 120                 125

Asp Ala Lys Val Asn Ile Asn Ala Thr Tyr Asn Gly Thr Arg Glu Glu
    130                 135                 140

Ile Lys Asn Cys Ser Phe Asn Ala Thr Thr Glu Leu Arg Asp Lys Lys
145                 150                 155                 160

Lys Lys Glu Tyr Ala Leu Phe Tyr Arg Leu Asp Ile Val Pro Leu Asn
                165                 170                 175

Lys Glu Gly Asn Asn Asn Ser Glu Tyr Arg Leu Ile Asn Cys Asn Thr
            180                 185                 190

Ser Val Ile Thr Gln Ala Cys Pro Lys Val Thr Phe Asp Pro Ile Pro
        195                 200                 205

Ile His Tyr Cys Ala Pro Ala Gly Tyr Ala Ile Leu Lys Cys Asn Asn
    210                 215                 220

Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Ile Ile Ile Arg Ser Glu Asn Leu Thr
            260                 265                 270

Asp Asn Val Lys Thr Ile Ile Val His Leu Asn Glu Ser Val Glu Ile
        275                 280                 285

Asn Cys Thr Arg Pro Asn Asn Asn Thr Arg Lys Ser Ile Arg Ile Gly
    290                 295                 300

Pro Gly Gln Thr Phe Tyr Ala Thr Gly Asp Ile Ile Gly Asp Ile Arg
305                 310                 315                 320

Gln Ala His Cys Asn Ile Ser Glu Ile Lys Trp Glu Lys Thr Leu Gln
                325                 330                 335

Arg Val Ser Glu Lys Leu Arg Glu His Phe Asn Lys Thr Ile Ile Phe
            340                 345                 350

Asn Gln Ser Ser Gly Gly Asp Leu Glu Ile Thr Thr His Ser Phe Asn
        355                 360                 365

```
Cys Gly Gly Glu Phe Phe Tyr Cys Asn Thr Ser Asp Leu Phe Asn
    370                 375                 380

Lys Thr Phe Asp Glu Thr Tyr Ser Thr Gly Ser Asn Ser Thr Asn Ser
385                 390                 395                 400

Thr Ile Thr Leu Pro Cys Arg Ile Lys Gln Ile Ile Asn Met Trp Gln
                405                 410                 415

Glu Val Gly Arg Ala Met Tyr Ala Ser Pro Ile Ala Gly Glu Ile Thr
                420                 425                 430

Cys Lys Ser Asn Ile Thr Gly Leu Leu Leu Thr Arg Asp Gly Gly
            435                 440                 445

Asn Asn Ser Thr Glu Glu Thr Phe Arg Pro Gly Gly Gly Asn Met Arg
450                 455                 460

Asp Asn Trp Arg Ser Glu Leu Tyr Lys Tyr Lys Val Val Glu Val Lys
465                 470                 475                 480

Pro Leu Gly Ile Ala Pro Thr Glu Ala Arg Arg Val Val Gln Lys
                485                 490                 495

Glu Lys Arg Ala Val Val Gly Leu Gly Ala Val Phe Leu Gly Phe Leu
            500                 505                 510

Gly Thr Ala Gly Ser Thr Met Gly Ala Ala Ser Ile Thr Leu Thr Val
        515                 520                 525

Gln Ala Arg Gln Leu Leu Ser Gly Ile Val Gln Gln Gln Ser Asn Leu
    530                 535                 540

Leu Arg Ala Ile Glu Ala Gln Gln His Met Leu Gln Leu Thr Val Trp
545                 550                 555                 560

Gly Ile Lys Gln Leu Gln Ala Arg Val Leu Ala Ile Glu Arg Tyr Leu
                565                 570                 575

Lys Asp Gln Gln Leu Leu Gly Met Trp Gly Cys Ser Gly Lys Leu Ile
            580                 585                 590

Cys Thr Thr Asn Val Tyr Trp Asn Ser Ser Trp Ser Asn Lys Thr Tyr
        595                 600                 605

Asn Glu Ile Trp Asp Asn Met Thr Trp Met Gln Trp Asp Arg Glu Ile
    610                 615                 620

Asp Asn Tyr Thr Asp Thr Ile Tyr Lys Leu Leu Glu Val Ser Gln Lys
625                 630                 635                 640

Gln Gln Glu Ser Asn Glu Lys Asp Leu Leu Ala Leu Asp Ser Trp Asn
                645                 650                 655

Asn Leu Trp Asn Trp Phe Asp Ile Ser Lys Trp Leu Trp Tyr Ile Lys
            660                 665                 670

Ile Phe Ile Met Ile Val Gly Gly Leu Ile Gly Leu Arg Ile Phe
        675                 680                 685

Ala Val Leu Ser Leu Val Asn Arg Val Arg Gln Gly Tyr Ser Pro Leu
    690                 695                 700

Ser Phe Gln Thr Leu Thr Pro Asn Pro Arg Glu Leu Asp Arg Leu Gly
705                 710                 715                 720

Gly Ile Glu Glu Glu Gly Gly Glu Gln Asp Arg Asp Arg Ser Ile Arg
                725                 730                 735

Leu Val Ser Gly Phe Phe Ser Leu Ala Trp Asn Asp Leu Arg Ser Leu
            740                 745                 750

Cys Leu Phe Cys Tyr His Arg Leu Arg Asp Phe Ile Leu Ile Ala Gly
        755                 760                 765

Arg Ala Val Glu Leu Leu Gly Arg Ser Ser Leu Gln Gly Leu Gln Arg
    770                 775                 780

Gly Trp Glu Ile Leu Lys Tyr Leu Gly Ser Leu Val Gln Tyr Trp Gly
```

```
                785                 790                 795                 800
Leu Glu Leu Lys Lys Ser Ala Ile Asn Leu Phe Asp Thr Ile Ala Ile
                    805                 810                 815

Ala Val Ala Glu Gly Thr Asp Arg Ile Ile Glu Glu Phe Leu Gln Arg
                820                 825                 830

Ile Val Arg Ala Ile Leu His Ile Pro Arg Arg Ile Arg Gln Gly Phe
                835                 840                 845

Glu Ala Ala Leu Gln
    850

<210> SEQ ID NO 15
<211> LENGTH: 192
<212> TYPE: DNA
<213> ORGANISM: Human immunodeficiency virus

<400> SEQUENCE: 15
atgacagtga cggggacatg gaggaattat caacaatggt ggatatgggg aatcttaggc       60
ttttggatgc taatgatttg taatggcttg tgggttacag tctactatgg ggtacctgtg      120
tggagagaag caaaaactac tctatttttgt gcctcagacg ctaaatcata tgagaaagag      180
gtgcataatg tc                                                          192

<210> SEQ ID NO 16
<211> LENGTH: 499
<212> TYPE: PRT
<213> ORGANISM: Human immunodeficiency virus

<400> SEQUENCE: 16

Met Thr Val Thr Gly Thr Trp Arg Asn Tyr Gln Gln Trp Trp Ile Trp
1               5                   10                  15

Gly Ile Leu Gly Phe Trp Met Leu Met Ile Cys Asn Gly Leu Trp Val
                20                  25                  30

Thr Val Tyr Tyr Gly Val Pro Val Trp Arg Glu Ala Lys Thr Thr Leu
            35                  40                  45

Phe Cys Ala Ser Asp Ala Lys Ser Tyr Glu Lys Glu Val His Asn Val
        50                  55                  60

Trp Ala Thr His Ala Cys Val Pro Thr Asp Pro Asn Pro Gln Glu Leu
65                  70                  75                  80

Val Leu Lys Asn Val Thr Glu Asn Phe Asn Met Trp Lys Asn Asp Met
                85                  90                  95

Val Asp Gln Met His Glu Asp Ile Ile Ser Leu Trp Asp Gln Ser Leu
                100                 105                 110

Lys Pro Cys Val Lys Leu Thr Pro Leu Cys Val Thr Leu Asn Cys Ser
            115                 120                 125

Asp Ala Lys Val Asn Ile Asn Ala Thr Tyr Asn Gly Thr Arg Glu Glu
        130                 135                 140

Ile Lys Asn Cys Ser Phe Asn Ala Thr Glu Leu Arg Asp Lys Lys
145                 150                 155                 160

Lys Lys Glu Tyr Ala Leu Phe Tyr Arg Leu Asp Ile Val Pro Leu Asn
                165                 170                 175

Lys Glu Gly Asn Asn Asn Ser Glu Tyr Arg Leu Ile Asn Cys Asn Thr
            180                 185                 190

Ser Val Ile Thr Gln Ala Cys Pro Lys Val Thr Phe Asp Pro Ile Pro
        195                 200                 205

Ile His Tyr Cys Ala Pro Ala Gly Tyr Ala Ile Leu Lys Cys Asn Asn
    210                 215                 220
```

| | | | | | | | | | | | |
|---|---|---|---|---|---|---|---|---|---|---|---|
| Lys | Thr | Phe | Asn | Gly | Thr | Gly | Pro | Cys | Asn | Asn | Val | Ser | Thr | Val | Gln |
| 225 | | | | 230 | | | | 235 | | | | 240 | | | |

```
Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Ile Ile Ile Arg Ser Glu Asn Leu Thr
        260                 265                 270

Asp Asn Val Lys Thr Ile Ile Val His Leu Asn Glu Ser Val Glu Ile
            275                 280                 285

Asn Cys Thr Arg Pro Asn Asn Thr Arg Lys Ser Ile Arg Ile Gly
    290                 295                 300

Pro Gly Gln Thr Phe Tyr Ala Thr Gly Asp Ile Ile Gly Asp Ile Arg
305                 310                 315                 320

Gln Ala His Cys Asn Ile Ser Glu Ile Lys Trp Glu Lys Thr Leu Gln
                325                 330                 335

Arg Val Ser Glu Lys Leu Arg Glu His Phe Asn Lys Thr Ile Ile Phe
            340                 345                 350

Asn Gln Ser Ser Gly Gly Asp Leu Glu Ile Thr Thr His Ser Phe Asn
        355                 360                 365

Cys Gly Gly Glu Phe Phe Tyr Cys Asn Thr Ser Asp Leu Phe Phe Asn
370                 375                 380

Lys Thr Phe Asp Glu Thr Tyr Ser Thr Gly Ser Asn Ser Thr Asn Ser
385                 390                 395                 400

Thr Ile Thr Leu Pro Cys Arg Ile Lys Gln Ile Ile Asn Met Trp Gln
                405                 410                 415

Glu Val Gly Arg Ala Met Tyr Ala Ser Pro Ile Ala Gly Glu Ile Thr
            420                 425                 430

Cys Lys Ser Asn Ile Thr Gly Leu Leu Leu Thr Arg Asp Gly Gly Gly
        435                 440                 445

Asn Asn Ser Thr Glu Glu Thr Phe Arg Pro Gly Gly Gly Asn Met Arg
450                 455                 460

Asp Asn Trp Arg Ser Glu Leu Tyr Lys Tyr Lys Val Val Glu Val Lys
465                 470                 475                 480

Pro Leu Gly Ile Ala Pro Thr Glu Ala Arg Arg Val Val Gln Lys
                485                 490                 495

Glu Lys Arg
```

<210> SEQ ID NO 17
<211> LENGTH: 1380
<212> TYPE: DNA
<213> ORGANISM: Artificial sequence
<220> FEATURE:
<223> OTHER INFORMATION: Nucleotide sequence for RVFV LPH-ptGn antigen

<400> SEQUENCE: 17

```
accggtatgg agtggagctg gatcttcttg ttcttgctca gcggcactgc aggtgttcac      60
tccatggatc ctcaccttag gaatagacct ggaaaaggtc ataactatat tgatggaatg     120
actcaagagg atgctacttg taagccagtg acttacgctg gagcatgctc ttcatttgat     180
gttcttttgg agaagggtaa atttcctttg ttccagtctt atgcacatca caggacatta     240
ctcgaagctg ttcatgatac tattatcgct aaagcagatc caccttcctg tgatttgcaa     300
tctgctcacg gaaatccttg catgaaggaa aaacttgtga tgaaaacaca ttgtccaaac     360
gattatcaga gcgcacacta cttgaataac gatggaaaga tggctagtgt taaatgccca     420
cctaagtacg agttgacaga agattgtaac ttctgcagac aaatgactgg agcatcactt     480
```

```
aagaaaggta gttacccatt gcaagatttg ttttgtcaga gtagcgagga tgatggatca    540
aagcttaaaa caaagatgaa aggagtttgt gaagttggtg tgcaagcttt gaagaaatgc    600
gatggacagt tatctactgc acatgaagtt gtgccttttg ctgttttcaa aaactctaag    660
aaagtgtatt tggataaact cgatcttaag actgaagaga accttttgcc agattcattt    720
gtttgtttcg agcacaaagg acaatacaag ggtactatgg atagtggtca gactaaaagg    780
gaacttaagt cattcgatat cagtcaatgt cctaagatag gaggtcatgg atccaagaaa    840
tgcactggag atgctgcatt tgttctgca tatgaatgca ctgctcagta tgctaatgca    900
tactgtagcc acgcaaacgg atccggtgtt gtgcaaattc aggtttctgg agtgtggaag    960
aaacctttgt gcgtgggtta cgagagagtt gtggttaaaa gggaactttc agctaagcct   1020
attcaaagag ttgagccatg tactacatgc atcacaaaat gtgaaccaca tggattggtg   1080
gttaggtcta ctggttttaa gatttcctct gctgttgcat gtgcttctgg agtttgcgtg   1140
actggtagcc aatccccttc tactgaaata cacttaagt atccaggaat ctcacagtca   1200
agtggaggag atattggtgt tcatatggca cacgatgatc aaagtgttag ctccaagatt   1260
gtggctcatt gtccacctca ggatccatgc cttgttcatg gatgtatagt gtgcgctcac   1320
ggtctcatta attatcaatg tcacacagca ctttctgctt aaaggcctcc cgggctcgag   1380
```

<210> SEQ ID NO 18
<211> LENGTH: 471
<212> TYPE: PRT
<213> ORGANISM: Artificial sequence
<220> FEATURE:
<223> OTHER INFORMATION: Amino acid sequence for RVFV LPH-ptGn antigen

<400> SEQUENCE: 18

```
Met Glu Thr Glu Trp Ser Trp Ile Phe Leu Phe Leu Leu Ser Gly Thr
1               5                   10                  15

Ala Gly Val His Ser Met Glu Thr Asp Pro His Leu Arg Asn Arg Pro
            20                  25                  30

Gly Lys Gly His Asn Tyr Ile Asp Gly Met Glu Thr Thr Gln Glu Asp
        35                  40                  45

Ala Thr Cys Lys Pro Val Thr Tyr Ala Gly Ala Cys Ser Ser Phe Asp
    50                  55                  60

Val Leu Leu Glu Lys Gly Lys Phe Pro Leu Phe Gln Ser Tyr Ala His
65                  70                  75                  80

His Arg Thr Leu Leu Glu Ala Val His Asp Thr Ile Ile Ala Lys Ala
                85                  90                  95

Asp Pro Pro Ser Cys Asp Leu Gln Ser Ala His Gly Asn Pro Cys Met
            100                 105                 110

Glu Thr Lys Glu Lys Leu Val Met Glu Thr Lys Thr His Cys Pro Asn
        115                 120                 125

Asp Tyr Gln Ser Ala His Tyr Leu Asn Asn Asp Gly Lys Met Glu Thr
    130                 135                 140

Ala Ser Val Lys Cys Pro Pro Lys Tyr Glu Leu Thr Glu Asp Cys Asn
145                 150                 155                 160

Phe Cys Arg Gln Met Glu Thr Thr Gly Ala Ser Leu Lys Lys Gly Ser
                165                 170                 175

Tyr Pro Leu Gln Asp Leu Phe Cys Gln Ser Ser Glu Asp Asp Gly Ser
            180                 185                 190

Lys Leu Lys Thr Lys Met Glu Thr Lys Gly Val Cys Glu Val Gly Val
        195                 200                 205
```

Gln Ala Leu Lys Lys Cys Asp Gly Gln Leu Ser Thr Ala His Glu Val
    210                 215                 220

Val Pro Phe Ala Val Phe Lys Asn Ser Lys Lys Val Tyr Leu Asp Lys
225                 230                 235                 240

Leu Asp Leu Lys Thr Glu Glu Asn Leu Leu Pro Asp Ser Phe Val Cys
                245                 250                 255

Phe Glu His Lys Gly Gln Tyr Lys Gly Thr Met Glu Thr Asp Ser Gly
            260                 265                 270

Gln Thr Lys Arg Glu Leu Lys Ser Phe Asp Ile Ser Gln Cys Pro Lys
        275                 280                 285

Ile Gly Gly His Gly Ser Lys Cys Thr Gly Asp Ala Ala Phe Cys
    290                 295                 300

Ser Ala Tyr Glu Cys Thr Ala Gln Tyr Ala Asn Ala Tyr Cys Ser His
305                 310                 315                 320

Ala Asn Gly Ser Gly Val Val Gln Ile Gln Val Ser Gly Val Trp Lys
                325                 330                 335

Lys Pro Leu Cys Val Gly Tyr Glu Arg Val Val Lys Arg Glu Leu
            340                 345                 350

Ser Ala Lys Pro Ile Gln Arg Val Glu Pro Cys Thr Thr Cys Ile Thr
        355                 360                 365

Lys Cys Glu Pro His Gly Leu Val Val Arg Ser Thr Gly Phe Lys Ile
370                 375                 380

Ser Ser Ala Val Ala Cys Ala Ser Gly Val Cys Val Thr Gly Ser Gln
385                 390                 395                 400

Ser Pro Ser Thr Glu Ile Thr Leu Lys Tyr Pro Gly Ile Ser Gln Ser
                405                 410                 415

Ser Gly Gly Asp Ile Gly Val His Met Glu Thr Ala His Asp Asp Gln
            420                 425                 430

Ser Val Ser Ser Lys Ile Val Ala His Cys Pro Pro Gln Asp Pro Cys
        435                 440                 445

Leu Val His Gly Cys Ile Val Cys Ala His Gly Leu Ile Asn Tyr Gln
450                 455                 460

Cys His Thr Ala Leu Ser Ala
465                 470

<210> SEQ ID NO 19
<211> LENGTH: 20
<212> TYPE: DNA
<213> ORGANISM: Artificial sequence
<220> FEATURE:
<223> OTHER INFORMATION: Primer sequence of 15-0552 Forward

<400> SEQUENCE: 19
ttcttcttct tgctgattgg                                                20

<210> SEQ ID NO 20
<211> LENGTH: 18
<212> TYPE: DNA
<213> ORGANISM: Artificial sequence
<220> FEATURE:
<223> OTHER INFORMATION: Primer sequence of 15-0553 Reverse

<400> SEQUENCE: 20
cacagaaaac cgctcacc                                                  18

<210> SEQ ID NO 21
<211> LENGTH: 4

```
<212> TYPE: PRT
<213> ORGANISM: Human immunodeficiency virus

<400> SEQUENCE: 21

Arg Glu Lys Arg
1

<210> SEQ ID NO 22
<211> LENGTH: 10
<212> TYPE: PRT
<213> ORGANISM: Artificial sequence
<220> FEATURE:
<223> OTHER INFORMATION: Flexible linker peptide (GGGGS)2

<400> SEQUENCE: 22

Gly Gly Gly Gly Ser Gly Gly Gly Gly Ser
1               5                   10
```